US012805835B2

(12) United States Patent
Soleimani et al.

(10) Patent No.: US 12,805,835 B2
(45) Date of Patent: Nov. 24, 2026

(54) APPARATUSES AND METHODS FOR CONFIGURING ULTRASOUND DEVICES

(71) Applicant: BFLY OPERATIONS, INC., Burlington, MA (US)

(72) Inventors: Hamid Soleimani, Guilford, CT (US); Nevada J. Sanchez, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 189 days.

(21) Appl. No.: 18/938,614

(22) Filed: Nov. 6, 2024

(65) Prior Publication Data

US 2025/0057505 A1 Feb. 20, 2025

Related U.S. Application Data

(63) Continuation of application No. 17/710,697, filed on Mar. 31, 2022, now Pat. No. 12,156,762.

(60) Provisional application No. 63/169,857, filed on Apr. 1, 2021.

(51) Int. Cl.
*A61B 8/12* (2006.01)
*A61B 8/00* (2006.01)

(52) U.S. Cl.
CPC .............. *A61B 8/12* (2013.01); *A61B 8/5207* (2013.01); *A61B 8/54* (2013.01)

(58) Field of Classification Search
None
See application file for complete search history.

(56) References Cited

U.S. PATENT DOCUMENTS

| | | | |
|---|---|---|---|
| 5,316,965 | A | 5/1994 | Philipossian et al. |
| 5,330,920 | A | 7/1994 | Soleimani et al. |
| 5,385,630 | A | 1/1995 | Philipossian et al. |
| 5,581,517 | A | 12/1996 | Gee et al. |
| 5,596,218 | A | 1/1997 | Soleimani et al. |
| 5,617,862 | A | 4/1997 | Cole et al. |
| 5,905,692 | A | 5/1999 | Dolazza et al. |
| 6,120,449 | A | 9/2000 | Snyder et al. |
| 6,506,160 | B1 | 1/2003 | Van Stralen et al. |
| 7,775,982 | B2 | 8/2010 | Hazard et al. |
| 7,941,908 | B2 | 5/2011 | Phelps et al. |
| 8,096,951 | B2 | 1/2012 | Kristoffersen et al. |

(Continued)

OTHER PUBLICATIONS

Bercoff, Jeremy, et al. "UltraFast™ Doppler." SuperSonic Imagine (2011). (Year: 2011).*

(Continued)

*Primary Examiner* — Jonathan D Armstrong
(74) *Attorney, Agent, or Firm* — Foley & Lardner LLP

(57) ABSTRACT

Ultrasound devices are described. The ultrasound devices may be flexibly configured to output a certain number of multilines per channel of ultrasound data and to process certain channels of ultrasound data per processing cycle. The ultrasound device may then be configured to either output more multilines per channel and process fewer channels per processing cycle, or output fewer multilines per channel and process more channels per processing cycle. In other words, the circuitry may be configured to change to a configuration with increased resolution and increased processing time or to a configuration with decreased resolution and decreased processing time.

20 Claims, 19 Drawing Sheets

(56) References Cited

U.S. PATENT DOCUMENTS

| | | | | |
|---|---|---|---|---|
| 8,137,272 | B2 * | 3/2012 | Cooley | G01S 7/52028 600/463 |
| 9,584,744 | B2 | 2/2017 | Lenchenkov et al. | |
| 9,667,889 | B2 | 5/2017 | Rothberg et al. | |
| 9,812,555 | B2 | 11/2017 | Madurawe et al. | |
| 9,910,140 | B2 | 3/2018 | Watanabe et al. | |
| 9,958,537 | B2 | 5/2018 | Chen et al. | |
| 10,082,488 | B2 | 9/2018 | Chen et al. | |
| 10,082,565 | B2 | 9/2018 | Chen et al. | |
| D846,128 | S | 4/2019 | de Jonge et al. | |
| 10,272,471 | B2 | 4/2019 | Alie et al. | |
| D847,738 | S | 5/2019 | Mastri et al. | |
| 10,371,804 | B2 | 8/2019 | Ralston et al. | |
| 10,398,414 | B2 | 9/2019 | Chen et al. | |
| 10,446,132 | B2 | 10/2019 | Alie et al. | |
| D867,752 | S | 11/2019 | de Jonge et al. | |
| 10,497,856 | B2 | 12/2019 | Rothberg et al. | |
| D876,636 | S | 2/2020 | de Jonge et al. | |
| D881,224 | S | 4/2020 | Elgena et al. | |
| D881,225 | S | 4/2020 | Elgena et al. | |
| D881,226 | S | 4/2020 | Elgena et al. | |
| D881,227 | S | 4/2020 | Elgena et al. | |
| D881,919 | S | 4/2020 | Elgena et al. | |
| 10,624,613 | B2 | 4/2020 | Ralston et al. | |
| D885,427 | S | 5/2020 | Elgena et al. | |
| D885,428 | S | 5/2020 | Elgena et al. | |
| D887,439 | S | 6/2020 | Elgena | |
| D887,562 | S | 6/2020 | de Jonge et al. | |
| D887,850 | S | 6/2020 | Elgena | |
| 10,672,974 | B2 | 6/2020 | Rothberg et al. | |
| 10,695,034 | B2 | 6/2020 | Ralston et al. | |
| 10,706,520 | B2 | 7/2020 | Rothberg et al. | |
| 10,707,201 | B2 | 7/2020 | Rothberg et al. | |
| 10,707,886 | B2 | 7/2020 | Chen et al. | |
| 10,709,415 | B2 | 7/2020 | Neben et al. | |
| 10,710,873 | B2 | 7/2020 | Rothberg et al. | |
| 10,755,692 | B2 | 8/2020 | Ralston et al. | |
| D899,077 | S | 10/2020 | de Jonge et al. | |
| 10,840,864 | B2 | 11/2020 | Singh et al. | |
| D903,694 | S | 12/2020 | Elgena et al. | |
| D903,709 | S | 12/2020 | Elgena | |
| 10,850,306 | B2 | 12/2020 | Rothberg et al. | |
| 10,856,844 | B2 | 12/2020 | Fife et al. | |
| 10,857,567 | B2 | 12/2020 | Singh et al. | |
| 10,893,850 | B2 | 1/2021 | Gafner et al. | |
| D909,048 | S | 2/2021 | de Jonge et al. | |
| 10,925,537 | B2 * | 2/2021 | Bailey | A61B 5/0024 |
| D914,356 | S | 3/2021 | de Jonge et al. | |
| D915,424 | S | 4/2021 | Elgena et al. | |
| 10,967,400 | B2 | 4/2021 | Alie et al. | |
| D918,960 | S | 5/2021 | Lane et al. | |
| D919,655 | S | 5/2021 | Elgena | |
| D919,656 | S | 5/2021 | Shin et al. | |
| 10,993,697 | B2 | 5/2021 | Rothberg et al. | |
| 11,005,435 | B2 | 5/2021 | Singh et al. | |
| 11,018,068 | B2 | 5/2021 | Liu et al. | |
| D923,637 | S | 6/2021 | Elgena et al. | |
| 11,020,053 | B2 * | 6/2021 | Bailey | A61F 2/12 |
| 11,045,139 | B2 * | 6/2021 | Bailey | H04W 4/70 |
| 11,048,334 | B2 | 6/2021 | Rothberg et al. | |
| 11,061,125 | B2 | 7/2021 | Chen et al. | |
| 11,375,980 | B2 | 7/2022 | Chen et al. | |
| 11,388,524 | B2 | 7/2022 | Lutsky et al. | |
| 11,435,458 | B2 | 9/2022 | Rothberg et al. | |
| 11,439,364 | B2 | 9/2022 | Rothberg et al. | |
| 11,446,001 | B2 | 9/2022 | Rothberg et al. | |
| 11,620,789 | B2 | 4/2023 | Hershkovich et al. | |
| 11,638,555 | B2 * | 5/2023 | Bailey | A61F 2/389 600/595 |
| 11,779,273 | B2 * | 10/2023 | Bailey | A61B 5/0002 600/595 |
| 11,896,391 | B2 * | 2/2024 | Bailey | A61B 5/0002 |
| 12,156,762 | B2 | 12/2024 | Soleimani | |
| 12,226,228 | B2 * | 2/2025 | Bailey | A61B 5/1122 |
| 12,285,267 | B2 * | 4/2025 | Bailey | A61B 5/0002 |
| 12,419,574 | B2 * | 9/2025 | Bailey | A61F 2/40 |
| 12,440,153 | B2 * | 10/2025 | Bailey | A61B 5/0002 |
| 2004/0267126 | A1 | 12/2004 | Takeuchi | |
| 2004/0267135 | A1 | 12/2004 | Takeuchi | |
| 2005/0113698 | A1 | 5/2005 | Kristoffersen et al. | |
| 2005/0203392 | A1 | 9/2005 | Peteresen et al. | |
| 2006/0058672 | A1 | 3/2006 | Klepper | |
| 2007/0016023 | A1 | 1/2007 | Phelps et al. | |
| 2008/0137482 | A1 | 6/2008 | Kang et al. | |
| 2008/0146938 | A1 | 6/2008 | Hazard et al. | |
| 2009/0007414 | A1 | 1/2009 | Phelps et al. | |
| 2009/0069692 | A1 * | 3/2009 | Cooley | G01S 7/52095 600/459 |
| 2010/0030076 | A1 | 2/2010 | Vortman et al. | |
| 2014/0187937 | A1 | 7/2014 | Liu et al. | |
| 2014/0243614 | A1 | 8/2014 | Rothberg et al. | |
| 2015/0039303 | A1 | 2/2015 | Lesso et al. | |
| 2015/0141831 | A1 | 5/2015 | Yamamoto et al. | |
| 2017/0100091 | A1 | 4/2017 | Eigil et al. | |
| 2017/0135676 | A1 | 5/2017 | Rothberg et al. | |
| 2018/0070917 | A1 | 3/2018 | Rothberg et al. | |
| 2019/0001159 | A1 | 1/2019 | Chen et al. | |
| 2019/0069842 | A1 | 3/2019 | Rothberg et al. | |
| 2019/0192072 | A1 * | 6/2019 | Bailey | A61F 2/389 |
| 2019/0282207 | A1 | 9/2019 | Chen et al. | |
| 2019/0343484 | A1 | 11/2019 | Rothberg et al. | |
| 2019/0350518 | A1 * | 11/2019 | Bailey | A61B 5/0002 |
| 2019/0350519 | A1 * | 11/2019 | Bailey | A61F 2/389 |
| 2019/0350520 | A1 * | 11/2019 | Bailey | H04W 4/70 |
| 2019/0350521 | A1 * | 11/2019 | Bailey | A61B 5/0024 |
| 2019/0350522 | A1 * | 11/2019 | Bailey | A61F 2/389 |
| 2019/0350523 | A1 * | 11/2019 | Bailey | A61F 2/12 |
| 2020/0093430 | A1 * | 3/2020 | Bailey | A61B 5/0024 |
| 2020/0093431 | A1 * | 3/2020 | Bailey | A61B 5/0002 |
| 2020/0098819 | A1 | 3/2020 | Lenchenkov et al. | |
| 2020/0315586 | A1 | 10/2020 | Sanchez | |
| 2020/0315592 | A1 | 10/2020 | Soleimani et al. | |
| 2020/0322454 | A1 | 10/2020 | Ersson et al. | |
| 2020/0383660 | A1 | 12/2020 | Rothberg et al. | |
| 2020/0390419 | A1 | 12/2020 | Neben et al. | |
| 2020/0400620 | A1 | 12/2020 | Rothberg et al. | |
| 2020/0405266 | A1 | 12/2020 | Yang et al. | |
| 2020/0405267 | A1 | 12/2020 | Yang et al. | |
| 2020/0405271 | A1 | 12/2020 | Chiu et al. | |
| 2021/0028792 | A1 | 1/2021 | Hwang et al. | |
| 2021/0048517 | A1 | 2/2021 | Bao et al. | |
| 2021/0056041 | A1 | 2/2021 | Sanchez | |
| 2021/0088638 | A1 | 3/2021 | Chen et al. | |
| 2021/0093291 | A1 | 4/2021 | Sanchez | |
| 2021/0114060 | A1 | 4/2021 | Rothberg et al. | |
| 2021/0124042 | A1 | 4/2021 | Fish et al. | |
| 2021/0167791 | A1 | 6/2021 | Hwang et al. | |
| 2021/0183832 | A1 | 6/2021 | Chen et al. | |
| 2021/0328564 | A1 | 10/2021 | Chen et al. | |
| 2021/0330295 | A1 | 10/2021 | Soleimani et al. | |
| 2021/0384872 | A1 | 12/2021 | Chen et al. | |
| 2021/0386399 | A1 | 12/2021 | Rothberg et al. | |
| 2022/0057497 | A1 | 2/2022 | Ralston et al. | |
| 2022/0079565 | A1 | 3/2022 | Bao et al. | |
| 2022/0087604 | A1 * | 3/2022 | Bailey | A61B 5/1114 |
| 2022/0087605 | A1 * | 3/2022 | Bailey | A61B 5/0002 |
| 2022/0087606 | A1 * | 3/2022 | Bailey | A61B 5/0002 |
| 2022/0104793 | A1 | 4/2022 | Sanchez et al. | |
| 2022/0110529 | A1 | 4/2022 | Rothberg et al. | |
| 2022/0171041 | A1 | 6/2022 | Chen et al. | |
| 2022/0361854 | A1 | 11/2022 | Maccio et al. | |
| 2023/0086731 | A1 * | 3/2023 | Bailey | A61F 2/3662 |
| 2023/0172538 | A1 * | 6/2023 | Bailey | A61B 5/1114 |
| 2023/0414170 | A1 * | 12/2023 | Bailey | A61F 2/12 |

OTHER PUBLICATIONS

Ricci, Stefano, et al. "Multi-line measurements of blood velocity vectors in real-time." 2016 IEEE International Ultrasonics Symposium (IUS). IEEE, 2016. (Year: 2016).*

(56) References Cited

OTHER PUBLICATIONS

Boni, Enrico, et al. "ULA-OP 256: A 256-channel open scanner for development and real-time implementation of new ultrasound methods." IEEE transactions on ultrasonics, ferroelectrics, and frequency control 63.10 (2016): 1488-1495. (Year: 2016).*
Boulos, Paul. Ultrasound imaging of the ultrasound thrombolysis. Diss. Université de Lyon, 2017. (Year: 2017).*
Kang, Jinbum, Won Seuk Jang, and Yangmo Yoo. "High PRF ultrafast sliding compound Doppler imaging: Fully qualitative and quantitative analysis of blood flow." Physics in Medicine & Biology 63.4 (2018): 045004. (Year: 2018).*
Ricci, Stefano, et al. "Real-time blood velocity vector measurement over a 2-D region." IEEE transactions on ultrasonics, ferroelectrics, and frequency control 65.2 (2017): 201-209. (Year: 2017).*
Lanza, Gregory M. "Ultrasound imaging: something old or something new?. " Investigative radiology 55.9 (2020): 573-577. (Year: 2020).*
Invitation to Pay Additional Fees mailed Jun. 3, 2022 in connection with International Application No. PCT/S22/22778.
International Search Report and Written Opinion mailed Aug. 3, 2022 in connection with International Application No. PCT/US22/22778.
Daft et al, Microfabricated Ultrasonic Transducers Monolithically Integrated with High Voltage Electronics. IEEE Ultrasonics Symposium conf 2004; DD. 493-496. 4 pages.
Daft et al., A matrix Transducer Design with Improved Image Quality and Acquisition Rate. IEEE Ultrasonics Symposium conf 2007; pp. 411-415. 5 pages.

* cited by examiner

APPARATUSES AND METHODS FOR CONFIGURING ULTRASOUND DEVICES

CROSS-REFERENCE TO RELATED APPLICATIONS

This application is a continuation of U.S. patent application Ser. No. 17/710,697 filed on Mar. 31, 2022, which claims the benefit of, and priority to U.S. Provisional Patent Application Ser. No. 63/169,857, filed on Apr. 1, 2021. The entire contents of the foregoing applications are incorporated by reference herein.

FIELD

Generally, the aspects of the technology described herein relate to ultrasound devices. Certain aspects relate to configuring ultrasound devices.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, an ultrasound device is provided, comprising control circuitry configured to: receive an indication to configure the ultrasound device in a first configuration that includes outputting m1 multilines per channel of ultrasound data and processing n1 channels of ultrasound data channels per processing cycle; configure the ultrasound device in the first configuration; receive an indication to configure the ultrasound device in a second configuration that includes outputting m2 multilines per channel of ultrasound data and processing n2 channels of ultrasound data channels per processing cycle; and configure the ultrasound device in the second configuration. In some embodiments, m2 is greater than m1 and n2 is less than n1, or m2 is less than m1 and n2 is greater than n1.

According to an aspect of the present application, an ultrasound device is provided, comprising: arbiter circuitry configured to receive multiple channels of ultrasound data; multiline processing units (MLs) configured to process channels of ultrasound data to produce multilines; and control circuitry configured to control which of the multiple channels of ultrasound data the arbiter circuitry outputs to which of the MLs on which processing cycle.

According to an aspect of the present application, an ultrasound device is provided, comprising: control circuitry; multiline processing units (MLs) configured to process channels of ultrasound data to produce multilines; and arbiter circuitry comprising multiplexers. Each of the multiplexers comprises: multiple input terminals each coupled to one of multiple channels of ultrasound data; a control terminal coupled to the control circuitry; and an output terminal coupled to a group of the MLs.

According to an aspect of the present application, an ultrasound device is provided, comprising: control circuitry; multiline processing units (MLs) configured to process channels of ultrasound data to produce multilines; and arbiter circuitry comprising arbiters. Each of the arbiters comprises: an internal node; a switch controlled by the control circuitry and coupled between the internal node and one of multiple channels of ultrasound data; a switch controlled by the control circuitry and coupled between the internal node and a group of the MLs; and at least one switch controlled by the control circuitry and coupled between the internal node and another one of the arbiters.

According to an aspect of the present application, an ultrasound device is provided, comprising: a semiconductor chip; multiline processing units (MLs) integrated on the semiconductor chip and configured to process channels of ultrasound data to produce multilines; and multiple power islands. The MLs comprise multiple groups of MLs, and each of the multiple groups of MLs is implemented in a different one of the multiple power islands.

According to an aspect of the present application, a method of operating an ultrasound device is provided, comprising: receiving, with control circuitry, an indication to configure the ultrasound device in a first configuration that includes outputting m1 multilines per channel of ultrasound data and processing n1 channels of ultrasound data channels per processing cycle, configuring the ultrasound device in the first configuration, then receiving, with the control circuitry, an indication to configure the ultrasound device in a second configuration that includes outputting m2 multilines per channel of ultrasound data and processing n2 channels of ultrasound data channels per processing cycle, and configuring the ultrasound device in the second configuration. In some embodiments, m2 is greater than m1 and n2 is less than n1, or m2 is less than m1 and n2 is greater than n1.

According to an aspect of the present application, a method of operating an ultrasound device is provided, comprising receiving multiple channels of ultrasound data with arbiter circuitry, processing channels of ultrasound data with multiline processing units (MLs) to produce multilines, and controlling, with control circuitry, which of the multiple channels of ultrasound data the arbiter circuitry outputs to which of the MLs on which processing cycle.

Some aspects include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1A:
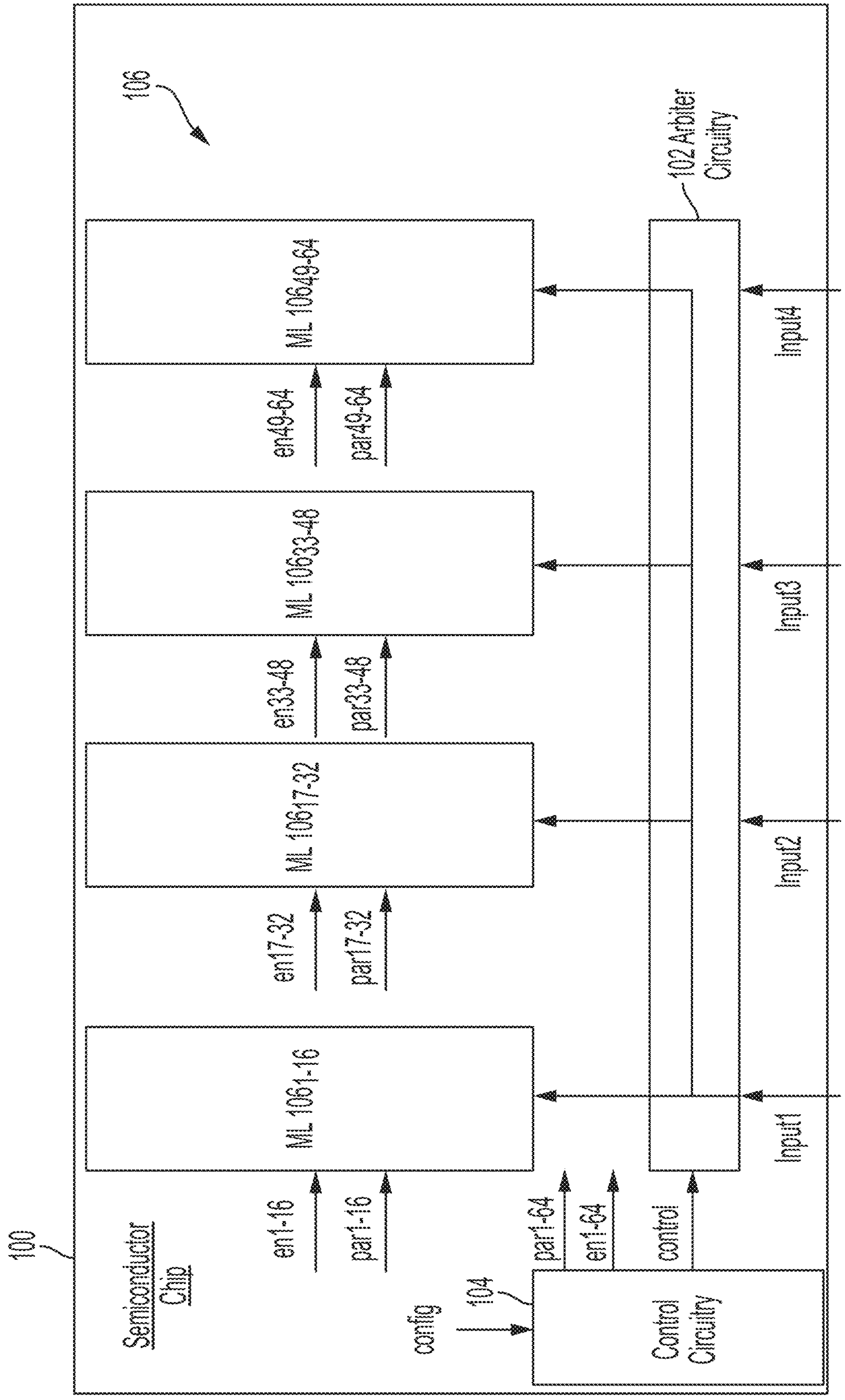
FIGS. 1A, 1B, 1C, and 1D illustrate schematic block diagrams of different processing cycles of circuitry in an ultrasound device configurable in multiple different configurations, in accordance with certain embodiments described herein.

In conventional ultrasound devices, the time it takes to process (e.g., to beamform) ultrasound data may be equal to the number of input channels of ultrasound data multiplied by the time required to process a single channel, regardless of the number of output multilines. A multiline may be a set of datapoints representing ultrasound scattering locations in space, where at least one datapoint of the multiline is formed from a combination of measurements from two or more ultrasound transducers such that the measurements from the two or more ultrasound transducers are calculated to be coming from the same spatial location. The number of output multilines may be one measure of the resolution of the output ultrasound data provided by the ultrasound device. Conventionally, the processing time is independent of the resolution as represented by the number of multilines.

In particular, even if the resolution—as represented by the number of output multilines—is reduced (e.g., due to limited communication bandwidth over a communication link), the time required to process the ultrasound data may not be reduced. This lack of ability to control the processing time performed by the ultrasound device may be undesirable in at least some situations in which different ultrasound applications may benefit from different processing times. Control over the processing time of the ultrasound device may provide greater versatility of the ultrasound device, and thus overall better performance of the ultrasound device. The inventors have developed circuitry and methods that allow for decreasing resolution while reducing processing time and therefore improving performance in that respect, or increasing resolution while increasing processing time. Thus, for applications where it may be desirable to reduce processing time, such as for imaging of the heart where it may be desirable to capture multiple ultrasound images during a single heartbeat, processing time may be reduced by reducing resolution. On the other hand, for applications where high resolution may be desirable and reduced processing time may not be critical, such as for imaging of the abdomen where there may be a large field-of-view, resolution may be increased by increasing processing time. In this manner, versatility and overall performance of the ultrasound device may be improved compared to conventional devices.

As will be described below, the inventors have developed control circuitry, arbiter circuitry, and processing units, where each of one or more processing units may be configured to output a particular unit of processed ultrasound data called a multiline. The arbiter circuitry may be configured to receive multiple channels of ultrasound data. The control circuitry may be configured to control which channels of ultrasound data the arbiter circuitry outputs to which of the processing units on which processing cycle based on a configuration parameter received by the control circuitry. In this manner, the control circuitry may flexibly configure the ultrasound device to output a certain number of multilines per channel of ultrasound data—and in so doing configure the ultrasound device to process the ultrasound data at a certain resolution—and to process certain channels of ultrasound data per processing cycle, and then configure the ultrasound device to either output more multilines per channel and process fewer channels per processing cycle, or output fewer multilines per channel and process more channels per processing cycle. In other words, the circuitry may be configured to change to a configuration with increased resolution and increased processing time or to a configuration with decreased resolution and decreased processing time. Such control may enhance the flexibility of the ultrasound device to perform optimally across a range of applications.

Various aspects of the present disclosure may be used alone, in combination, or in a variety of arrangements not explicit in the embodiments described in the foregoing. The various aspects are therefore not limited in their application to the details and arrangement of components set forth in the foregoing description or illustrated in the drawings. For example, aspects described in one embodiment may be combined in any manner with aspects described in other embodiments.

FIGS. 1A-3 illustrate schematic block diagrams of circuitry in an ultrasound device configurable in multiple different configurations, in accordance with certain embodiments described herein. The circuitry is integrated in a semiconductor chip 100 (or, in some embodiments, in multiple semiconductor chips) in the ultrasound device. The circuitry includes arbiter circuitry 102, control circuitry 104, and 64 multiline processing units (MLs) 106, referred to as ML $\mathbf{106}_1$, ML $\mathbf{106}_2$ . . . ML $\mathbf{106}_{64}$.

The arbiter circuitry 102 includes circuitry configured to receive multiple channels of ultrasound data and output particular channels of ultrasound data to particular MLs 106 on particular processing cycles. In the examples of FIGS. 1A-3, the arbiter circuitry 102 receives four channels of ultrasound data (referred to as $input_1$, $input_2$, $input_3$, and $input_4$). Each of the channels may be, for example, the output of an analog-to-digital converter (ADC) configured to convert analog ultrasound data from one or more particular ultrasound transducers in the ultrasound device, the output of an ultrasound processing unit (UPU) in the ultrasound device that may include one or more such ADCs, or the output of any other group of circuitry in the ultrasound device.

The control circuitry 104 receives a configuration parameter as an input (referred to as config) and outputs one or more control signals (referred to as control) to the arbiter circuitry 102. The control circuitry 104 may be configured to use the control signals to control the arbiter circuitry 102 to output particular channels of ultrasound data to particular MLs 106 on particular processing cycles based on the particular configuration parameter received. In other words, the control circuitry may be configured to control which channels of ultrasound data the arbiter circuitry 102 outputs to which of the MLs 106 on which processing cycle based on the configuration parameter config received by the control circuitry 104.

Each of the MLs 106 may be circuitry configured to receive a channel of ultrasound data as an input and project that channel's ultrasound data onto a particular portion of an ultrasound image (where the particular portion of the ultrasound image may be referred to as a multiline). This may be referred to as beamforming. The ultrasound device (or a processing device receiving data from the ultrasound device) may be configured to use the outputs of all the MLs 106 together to form an output ultrasound image.

The control circuitry 104 is further configured to output enable signals (labeled as $en_{1-64}$) to the MLs 106. Each of the MLs 106 may receive one of these enable signals. The control circuitry 104 may cause certain of the MLs 106 to be turned on or off by using the enable signals. For example, those MLs 106 receiving an enable signal that is digital high may be enabled, while those MLs 106 receiving an enable signal that is digital low may be disabled. Disabling certain MLs 106 may be helpful, for example, in conserving power.

The control circuitry 104 is further configured to output parameters (labeled as $par_{1-64}$) to the MLs 106. Each of the MLs 106 may receive at least one of these parameters. The control circuitry 104 may use the parameters to control the beamforming performed by each of the MLs 106. For example, the parameters may control focusing of each of the MLs 106 on particular points in space. The specific parameters outputted by the control circuitry 104 may be dependent on the particular configuration (i.e., dependent on config).

Figure 1B:
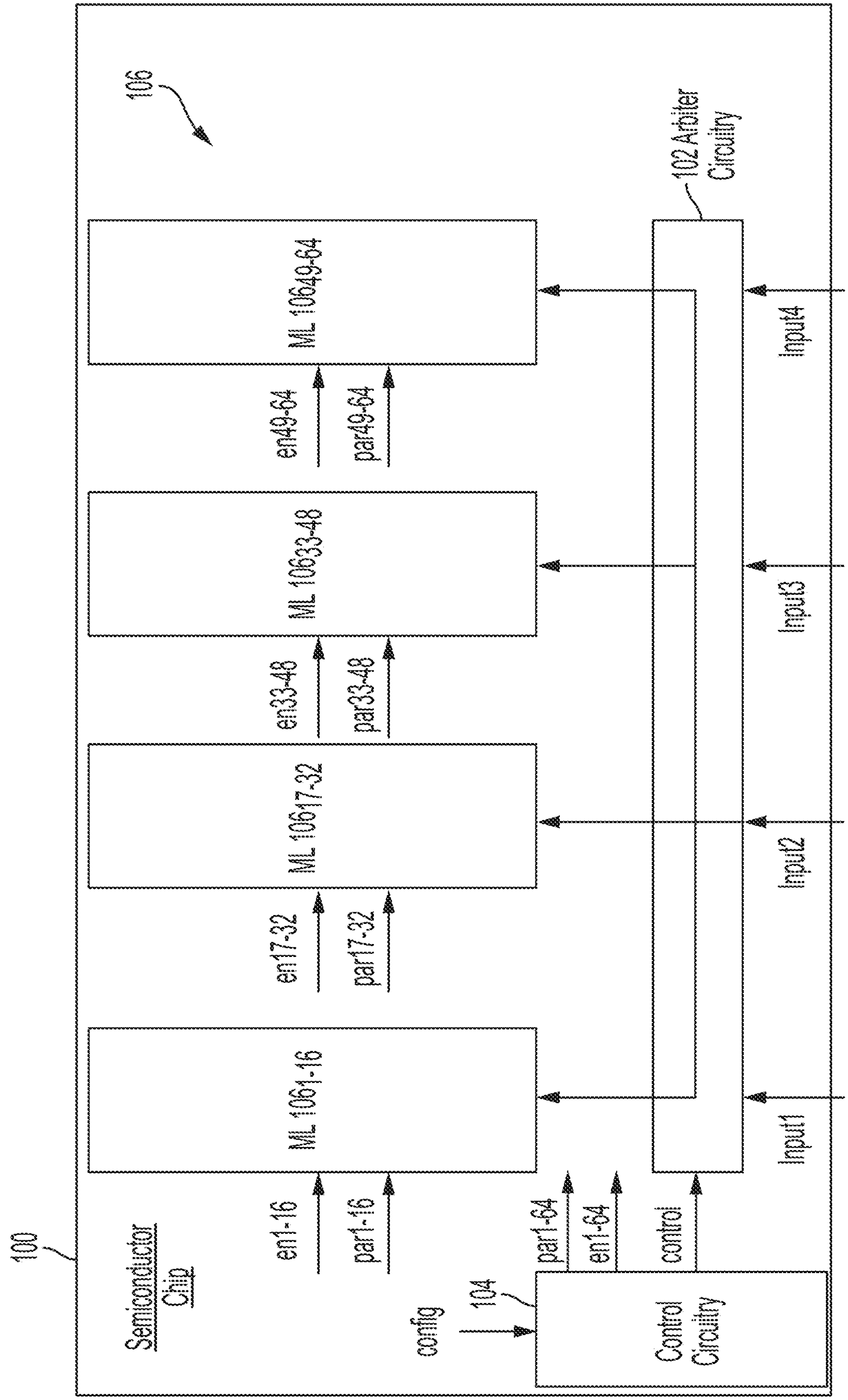
Figure 1C:
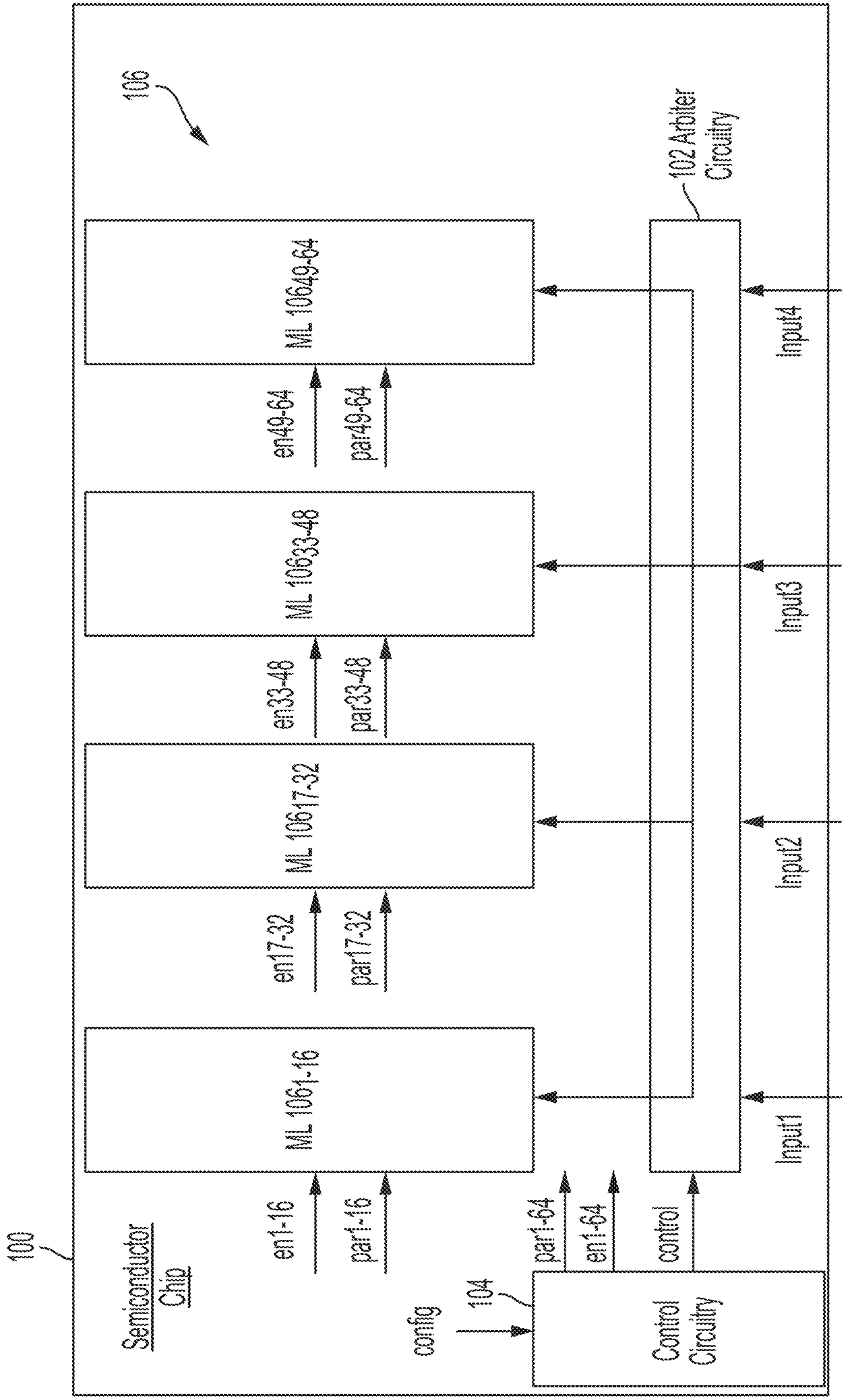
Figure 1D:
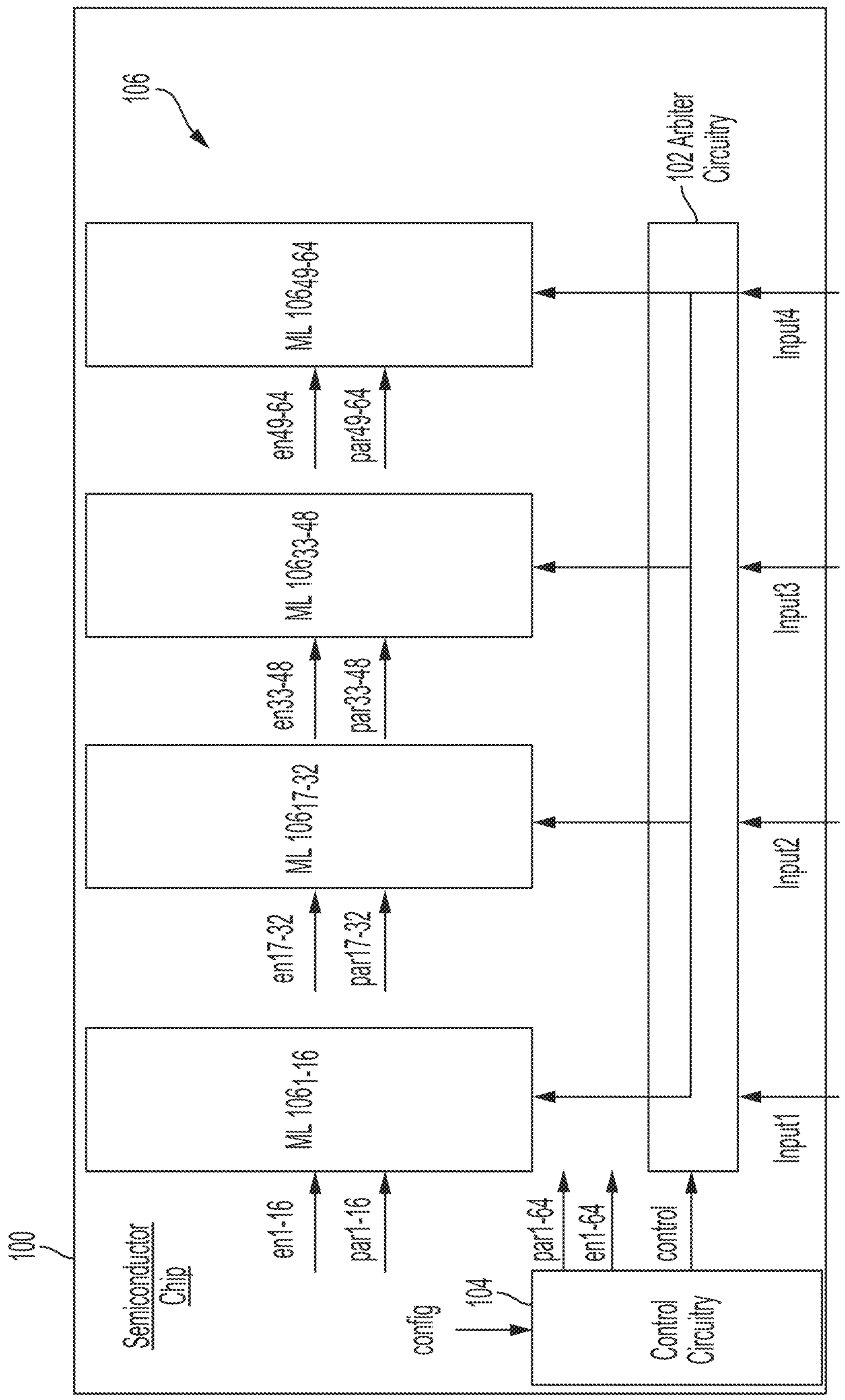

Referring to FIGS. 1A-1D, and assuming a configuration in which all the 64 MLs 106 are enabled, the arbiter circuitry 102 is configured, based on control signals received from the control circuitry 104, to output one channel of ultrasound data to each of the 64 MLs 106 for a given processing cycle. Thus, the 64 MLs 106 may be configured to together output 64 multilines per channel of ultrasound data. Each of the FIGS. 1A-1D illustrates a different processing cycle. As illustrated in FIG. 1A, the arbiter circuitry 102 may be configured to output the channel of ultrasound data $input_1$ to the 64 MLs 106 on a first processing cycle. Then as illustrated in FIG. 1B, the arbiter circuitry 102 may be configured to output $input_2$ to the 64 MLs 106 on a subsequent processing cycle. Then as illustrated in FIG. 1C, the arbiter circuitry 102 may be configured to output $input_3$ to the 64 MLs 106 on a subsequent processing cycle. Then as illustrated in FIG. 1D, the arbiter circuitry 102 may be configured to output $input_4$ to the 64 MLs 106 on a subsequent processing cycle. It may thus take four processing cycles for the ultrasound device to process all four channels of ultrasound data, where processing each of the four channels of ultrasound data may include outputting 64 multilines per channel of ultrasound data. Because this configuration involves processing one channel of ultrasound data at a time by 64 MLs 106, this configuration may be referred to as a 1×64 configuration. The control circuitry 104 may receive at config a particular configuration parameter specific to the 1×64 configuration, and based on this configuration parameter, output specific control signals at control to cause the arbiter circuitry 102 to output one channel in parallel to the 64 MLs 106 for each processing cycle.

Only enabling a portion of the MLs 106 expands the possible configurations. Between 1 and 64 MLs 106 may be disabled. If k MLs 106 are enabled, because the configurations of FIGS. 1A-1D involve processing one channel of ultrasound data at a time by k MLs 106, these configurations may be referred to as 1×k configurations, where k may be between 1 and 64.

Figure 2A:
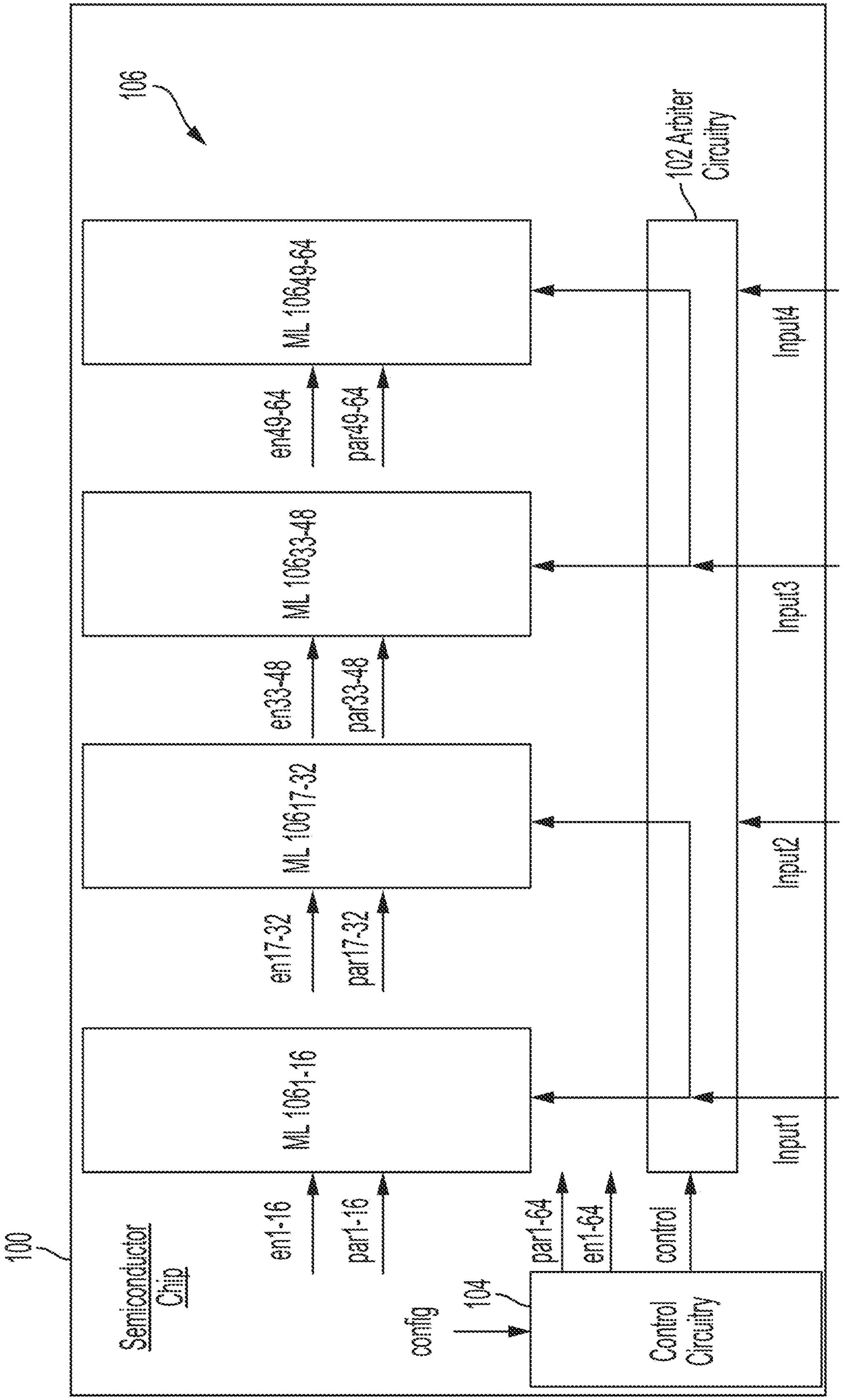
FIGS. 2A-2B illustrate schematic block diagrams of different processing cycles of circuitry in an ultrasound device configurable in multiple different configurations, in accordance with certain embodiments described herein.
Figure 2B:
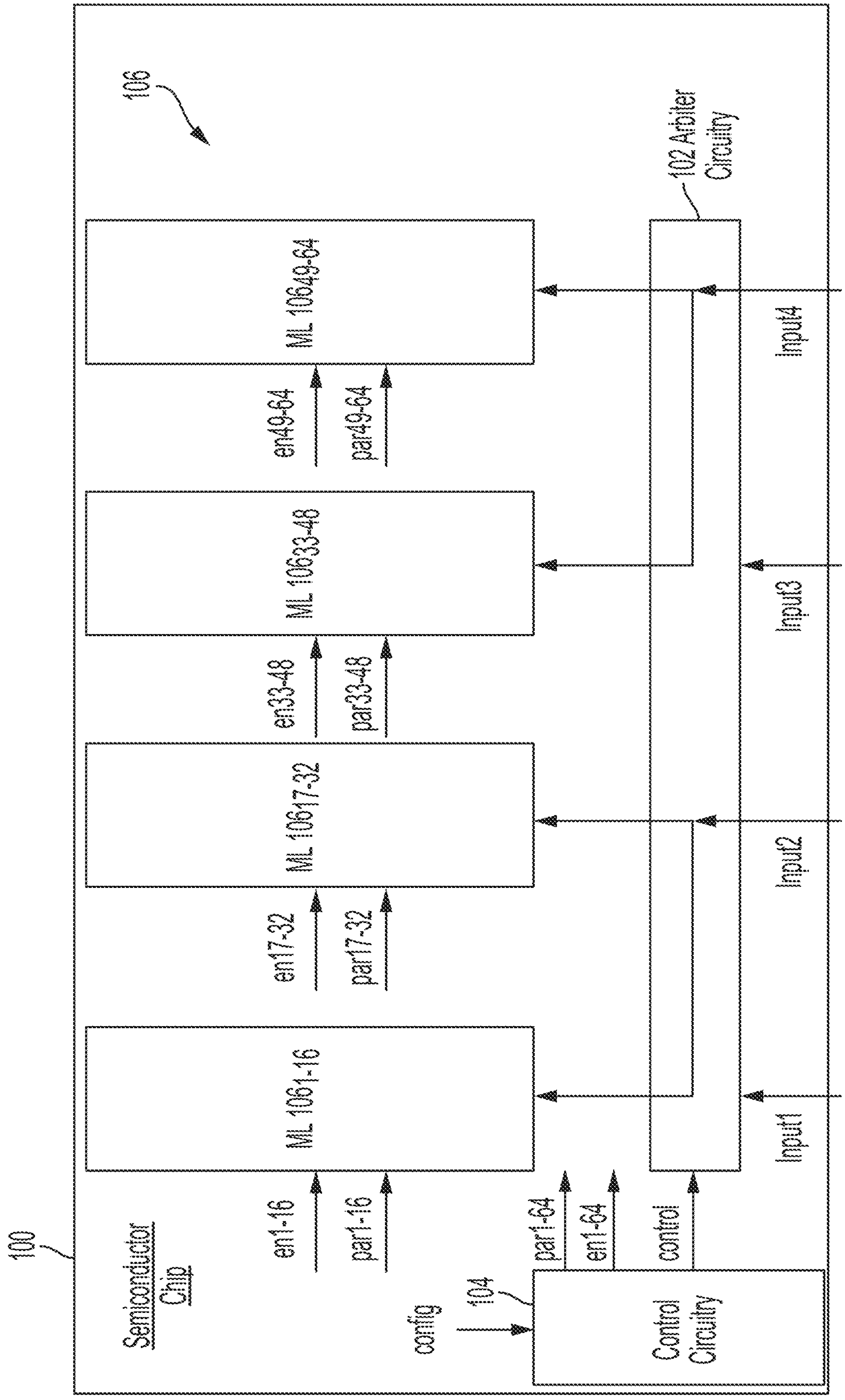

Referring to FIGS. 2A-2B, and assuming a configuration in which all the 64 MLs 106 are enabled, the arbiter circuitry 102 is configured, based on control signals received from the control circuitry 104, to output one channel of ultrasound data to each of 32 MLs 106 and another channel of ultrasound data to each of the other 32 MLs 106 for a given processing cycle. Thus, the 64 MLs 106 may be configured to together output 32 multilines per channel of ultrasound data. Each of FIGS. 2A-2B illustrates a different processing cycle. As illustrated in FIG. 2A, the arbiter circuitry 102 may be configured to output the channels of ultrasound data $input_1$ and $input_3$ to the 64 MLs 106, each channel being outputted to 32 of the 64 MLs 106, on a first processing cycle. Then as illustrated in FIG. 2B, the arbiter circuitry 102 may be configured to output $input_2$ and $input_4$ to the 64 MLs 106, each channel being outputted to 32 of the 64 MLs 106, on a subsequent processing cycle. The arbiter circuitry 102 may thus be configured to process two channels of ultrasound data in parallel, and it may thus take two processing cycles for the ultrasound device to process all four channels of ultrasound data, where processing each of the four channels of ultrasound data may include outputting 32 multilines per channel of ultrasound data. Because this configuration involves processing two channels of ultrasound data at a time by 32 MLs 106 each, this configuration may be referred to as a 2×32 configuration. The control circuitry 104 may receive at config a particular configuration parameter specific to the 2×32 configuration, and based on this configuration parameter, output specific control signals at control to cause the arbiter circuitry 102 to output two channels in parallel to 32 MLs 106 each for each processing cycle.

Only enabling a portion of the MLs 106 expands the possible configurations. Between 1 and 32 of $ML_{1-32}$ may be enabled and between 1 and 32 of $ML_{33-64}$ may be enabled. If k of $ML_{1-32}$ and k of $ML_{33-64}$ are enabled, because the configurations of FIGS. 2A-2B involve processing two channels of ultrasound data at a time by k MLs 106 each, these configurations may be referred to as a 2×k configurations, where k may be between 1 and 32.

Figure 3:
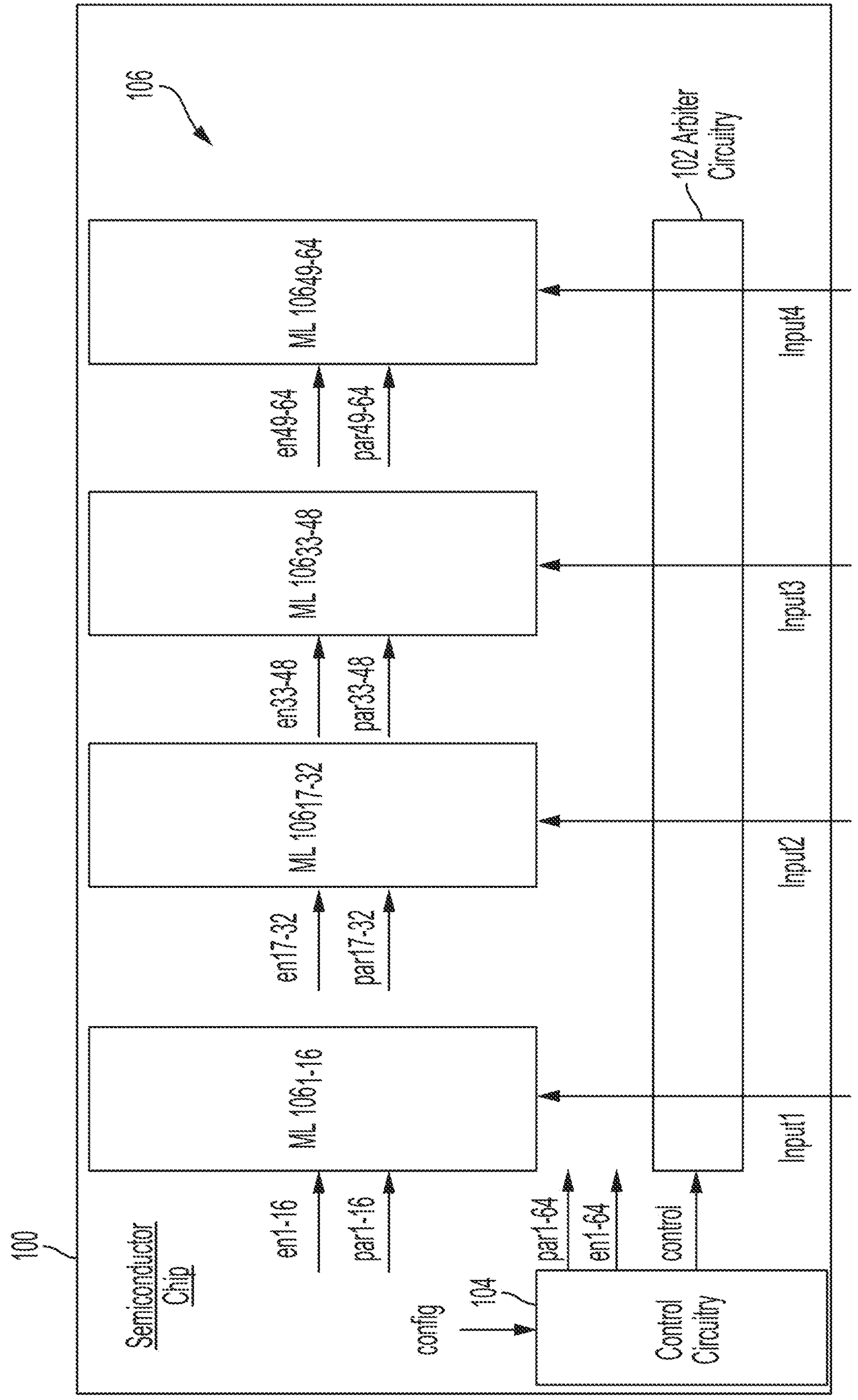
FIG. 3 illustrates a schematic block diagram of circuitry in an ultrasound device configurable in multiple different configurations, in accordance with certain embodiments described herein.

Referring to FIG. 3, and assuming a configuration in which all 64 MLs 106 are enabled, the arbiter circuitry 102 is configured, based on control signals received from the control circuitry 104, to output the channel of ultrasound data $input_1$ to each of 16 MLs 106, to output $input_2$ to each of another 16 MLs 106, to output $input_3$ to each of another 16 MLs 106, and to output $input_4$ to the other 16 MLs 106 for a given processing cycle. Thus, the 64 MLs 106 may be configured to together output 16 multilines per channel of ultrasound data. FIG. 3 illustrates a processing cycle. The arbiter circuitry 102 may be configured to output all four channels—$input_1$, $input_2$, $input_3$, and $input_4$—of ultrasound data to the 64 MLs 106, each channel being outputted to 16 of the 64 MLs 106, on each processing cycle. The arbiter circuitry 102 may thus be configured to process four channels of ultrasound data in parallel, and it may thus take one processing cycle for the ultrasound device to process all four channels of ultrasound data, where processing each of the four channels of ultrasound data may include outputting 16 multilines per channel of ultrasound data. Because this configuration involves processing four channels of ultrasound data at a time by 16 MLs 106 each, this configuration may be referred to as a 4×16 configuration. The control circuitry 104 may receive at config a particular configuration parameter specific to the 4×16 configuration, and based on this configuration parameter, output specific control signals at control to cause the arbiter circuitry 102 to output four channels in parallel to 16 MLs 106 each for each processing cycle.

Only enabling a portion of the MLs 106 expands the possible configurations. Between 1 and 16 of $ML_{1-16}$ may be enabled, between 1 and 16 of $ML_{17-32}$ may be enabled, between 1 and 16 of $ML_{33-48}$ may be enabled, and between 1 and 16 of $ML_{49-64}$ may be enabled. If k of $ML_{1-16}$, k of $ML_{17-32}$, k of $ML_{33-48}$, and k of $ML_{49-64}$ are enabled, because the configurations of FIG. 3 involve processing four channels of ultrasound data at a time by k MLs 106 each, these configuration may be referred to as a 4×k configuration, where k may be between 1 and 16.

Figure 4:
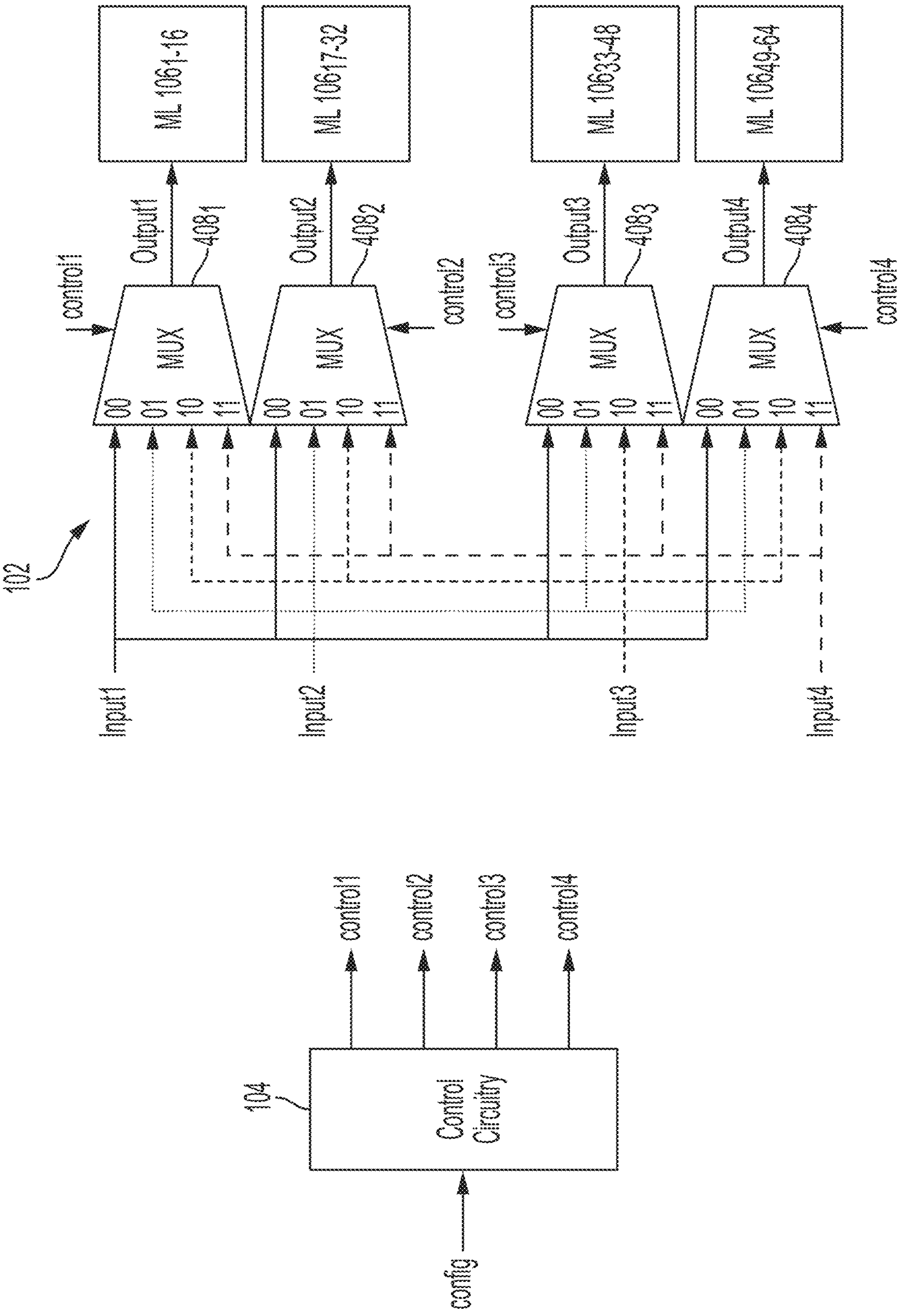
FIG. 4 illustrates the arbiter circuitry, control circuitry, and MLs of FIGS. 1A-3 in more detail.

FIG. 4 illustrates the arbiter circuitry 102, the control circuitry 104, and the MLs $\mathbf{106}_{1-64}$ in more detail. The arbiter circuitry 102 includes four multiplexers (MUX), multiplexer $\mathbf{408}_1$, multiplexer $\mathbf{408}_2$, multiplexer $\mathbf{408}_3$, and multiplexer $\mathbf{408}_4$. Each of the multiplexers receives as inputs at input terminals the four channels of ultrasound data, referred to as $input_1$, $input_2$, $input_3$, and $input_4$, as well as a control signal received from the control circuitry 104. The multiplexer $\mathbf{408}_1$ outputs at its output terminal one of the four channels of ultrasound data to the MLs $\mathbf{106}_{1-16}$ based on the control signal $control_1$ received at its control terminal, which is coupled to the control circuitry 104. The multiplexer $\mathbf{408}_2$ outputs at its output terminal one of the four channels of ultrasound data to the MLs $\mathbf{106}_{17-32}$ based on the control signal $control_2$ received at its control terminal, which is coupled to the control circuitry 104. The multiplexer $\mathbf{408}_3$ outputs at its output terminal one of the four channels of ultrasound data to the MLs $\mathbf{106}_{33-48}$ based on the control signal $control_3$ received at its control terminal, which is coupled to the control circuitry 104. The multiplexer $\mathbf{408}_4$ outputs at its output terminal one of the four channels of ultrasound data to the MLs $\mathbf{106}_{49-64}$ based on the control signal $control_4$ received at its control terminal, which is coupled to the control circuitry 104. (The signals $control_1$, $control_2$, $control_3$, and $control_4$ may be examples of the signal control illustrated in FIGS. 1A-3).

In the example of FIG. 4, each input terminal of each of the multiplexers $\mathbf{408}_1$-$\mathbf{408}_4$ is labeled with a two-bit value (00, 01, 10, or 11). Each of the multiplexers $\mathbf{408}_1$-$\mathbf{408}_4$ receives $input_1$ at input terminal 00, $input_2$ at input terminal 01, $input_3$ at input terminal 10, and $input_4$ at input terminal 11. If a given one of the multiplexers $\mathbf{408}_1$-$\mathbf{408}_4$ receives a control signal having a value 00, that multiplexer may be configured to output $input_1$. If a given one of the multiplexers $\mathbf{408}_1$-$\mathbf{408}_4$ receives a control signal having a value 01, that multiplexer may be configured to output $input_2$. If a given one of the multiplexers $\mathbf{408}_1$-$\mathbf{408}_4$ receives a control signal having a value 10, that multiplexer may be configured to output $input_3$. If a given one of the multiplexers $\mathbf{408}_1$-$\mathbf{408}_4$ receives a control signal having a value 11, that multiplexer may be configured to output $input_4$.

In operation, the control circuitry 104 may control how many parallel channels are outputted to how many MLs 106 based on the control signals outputted to the multiplexers $\mathbf{408}_1$-$\mathbf{408}_4$. Thus, for a 1×k configuration (i.e., one channel outputted at a time), the control circuitry 104 may output control signals such that each of the multiplexers $\mathbf{408}_1$-$\mathbf{408}_4$ outputs the same channel on a given processing cycle. For a 2×k configuration (i.e., two channels outputted in parallel at a time), the control circuitry 104 may output control signals such that two of the multiplexers (e.g., $\mathbf{408}_1$ and $\mathbf{408}_2$) output one channel and the other two multiplexers ($\mathbf{408}_3$-$\mathbf{408}_4$) output a different channel on a given processing cycle. For a 4×k configuration (i.e., four channels outputted in parallel at a time), the control circuitry 104 may output control signals such that each of the four multiplexers $\mathbf{408}_1$-$\mathbf{408}_4$ outputs a different channel on a given processing cycle. The control circuitry 104 may output particular control signals based on its received signal config, such that config controls the configuration. For example, if config has the value 00, then the control circuitry 104 may output control signals for a 1×k configuration. If config has the value 01, then the control circuitry 104 may output control signals for a 2×k configuration. If config has the value 10, then the control circuitry 104 may output control signals for a 4×k configuration. However, other schemes for config may be used instead. Table 1 illustrates in more detail example values of each of the control signals $control_1$, $control_2$, $control_3$, and $control_4$ for different processing cycles in different configurations:

TABLE 1

Values of each of the control signals for different processing cycles in different configurations.

| Configuration | Processing Cycle | $control_1$ | $control_2$ | $control_3$ | $control_4$ | Outputs |
|---|---|---|---|---|---|---|
| 1 × k | 1 | 00 | 00 | 00 | 00 | $Output_{1,2,3,4} = Input_1$ |
| | 2 | 01 | 01 | 01 | 01 | $Output_{1,2,3,4} = Input_2$ |
| | 3 | 10 | 10 | 10 | 10 | $Output_{1,2,3,4} = Input_3$ |
| | 4 | 11 | 11 | 11 | 11 | $Output_{1,2,3,4}$ = Input4 |
| 2 × k | 1 | 00 | 00 | 10 | 10 | $Output_{1,2} = Input_1$<br>$Output_{3,4} = Input_3$ |
| | 2 | 01 | 01 | 11 | 11 | $Output_{1,2} = Input_2$<br>$Output_{3,4} = Input_4$ |
| 4 × k | 1 | 00 | 01 | 10 | 11 | $Output_1 = Input_1$<br>$Output_2 = Input_2$<br>$Output_3 = Input_3$<br>$Output_4 = Input_4$ |

It should be appreciated that the above description is non-limiting, and some embodiments may use different schemes for the control signals $control_1$, $control_2$, $control_3$, and $control_4$ in order to enable the same functionality.

Generally, arbiter circuitry of the type illustrated in FIG. 4 may include multiple multiplexers (e.g., equal to the number of input channels of ultrasound data received by each multiplexer). Each of the multiplexers may be configured to receive as inputs each of the multiple channels of ultrasound data. Each of the multiplexers may be configured to output a channel to a respective (e.g., a different) group of MLs. Control circuitry may be configured to control each of the multiplexers (using the control signals) to output a particular one of the channels of ultrasound data to that multiplexer's respective group of MLs on a particular processing cycle. The control signals outputted by the control circuitry to each of the multiplexers on a given processing cycle may be based on the configuration parameter config received by the control circuitry. Generally, each of the multiplexers of the type illustrated in FIG. 4 may include multiple input terminals each coupled to one of multiple channels of ultrasound data, a control terminal coupled to the control circuitry, and an output terminal coupled to a group of the MLs.

FIGS. 5A-7 illustrate schematic block diagrams of circuitry in an ultrasound device configured with different configurations, in accordance with certain embodiments described herein. The circuitry is integrated in a semiconductor chip 500 (or in some embodiments, in multiple semiconductor chips) in the ultrasound device. The circuitry includes arbiter circuitry 502, control circuitry 504, and the 64 MLs 106. The arbiter circuitry 502 includes arbiters $\mathbf{502}_1$-$\mathbf{502}_4$. As will be described further below, the circuitry illustrated in FIGS. 5A-7 may be helpful, for example, in casing on-chip routing.

Generally, arbiter circuitry of the type illustrated in FIGS. 5A-7 may include multiple arbiters configured to receive a channel of ultrasound data from circuitry external to the arbiter circuitry (not illustrated). The control circuitry may be configured to control each of the arbiters (using the control signals) to do one, both, or none of the following:

1. Receive a channel of ultrasound data from other arbiters; and/or

2. Output one of the received channels of ultrasound data (received either from the external circuitry or from other arbiters) to other arbiters on particular processing cycles.

The control circuitry may control each of the arbiters (using the control signals) to output one of the received channels of ultrasound data (received either from the external circuitry or from other arbiters) to a particular group of MLs on particular processing cycles. Each of the arbiters may be configured to output a channel to a respective (e.g., a different) group of MLs. The control signals outputted by the control circuitry to each of the arbiters on a given processing cycle may be based on the configuration parameter config received by the control circuitry.

In the examples of FIGS. 5A-7, the arbiter $\mathbf{502}_1$ receives $input_1$ from circuitry external to the arbiter circuitry 502 (not illustrated), may receive a channel of ultrasound data from or output a channel of ultrasound data to the arbiter $\mathbf{502}_2$, and may output one of the received channels of ultrasound data to the MLs $\mathbf{106}_{1-16}$. The arbiter $\mathbf{502}_2$ receives $input_2$ from circuitry external to the arbiter circuitry 502 (not illustrated), may receive a channel of ultrasound data from or output a channel of ultrasound data to the arbiter $\mathbf{502}_1$, may receive a channel of ultrasound data from or output a channel of ultrasound data to the arbiter $\mathbf{502}_3$, and may output one of the received channels of ultrasound data to the MLs $\mathbf{106}_{17-32}$. The arbiter $\mathbf{502}_3$ receives $input_3$ from circuitry external to the arbiter circuitry 502 (not illustrated), may receive a channel of ultrasound data from or output a channel of ultrasound data to the arbiter $\mathbf{502}_2$, may receive a channel of ultrasound data from or output a channel of ultrasound data to the arbiter $\mathbf{502}_4$, and may output one of the received channels of ultrasound data to the MLs $\mathbf{106}_{33-48}$. The arbiter $\mathbf{502}_4$ receives $input_4$ from circuitry external to the arbiter circuitry 502 (not illustrated), may receive a channel of ultrasound data from or output a channel of ultrasound data to the arbiter $\mathbf{502}_3$, and may output one of the received channels of ultrasound data to the MLs $\mathbf{106}_{49-64}$.

The non-illustrated circuitry may be, and each of the channels may be the output of, for example, an analog-to-digital converter (ADC) configured to convert analog ultrasound data from one or more particular ultrasound transducers in the ultrasound device, an ultrasound processing unit (UPU) in the ultrasound device that may include one or more such ADCs, or any other group of circuitry in the ultrasound device.

The control circuitry 504 receives a configuration parameter as an input (referred to as config) and outputs control signals to the arbiters $\mathbf{502}_1$-$\mathbf{502}_4$. In the examples of FIGS. 5A-7, the control circuitry 504 outputs the control signal $control_1$ to the arbiter $\mathbf{502}_1$, the control signal $control_2$ to the arbiter $\mathbf{502}_2$, the control signal $control_3$ to the arbiter $\mathbf{502}_3$, and the control signal $control_4$ to the arbiter $\mathbf{502}_4$. The control circuitry 504 may be configured to use the control signals to control each of the arbiters $\mathbf{502}_1$-$\mathbf{502}_4$ to output its received channels of ultrasound data to particular MLs 106 or another of the arbiters $\mathbf{502}_1$-$\mathbf{502}_4$ on particular processing cycles based on the particular configuration parameter received. In other words, the control circuitry 504 may be configured to control which channels of ultrasound data each of the arbiters $\mathbf{502}_1$-$\mathbf{502}_4$ outputs to the MLs 106 which they are coupled to on which processing cycle based on a configuration parameter received by the control circuitry 504. Further description of the MLs 106 and the enable signals (labeled as $en_{1-64}$) may be found above.

Referring to FIGS. 5A-5D, and assuming a configuration in which all the 64 MLs 106 are enabled, the arbiters $\mathbf{502}_1$-$\mathbf{502}_4$ are configured to output one channel of ultrasound data to each of the 64 MLs 106 for a given processing cycle. Thus, the 64 MLs 106 may be configured to together output 64 multilines per channel of ultrasound data. Each of the FIGS. 5A-5D illustrates a different processing cycle.

Figure 5A:
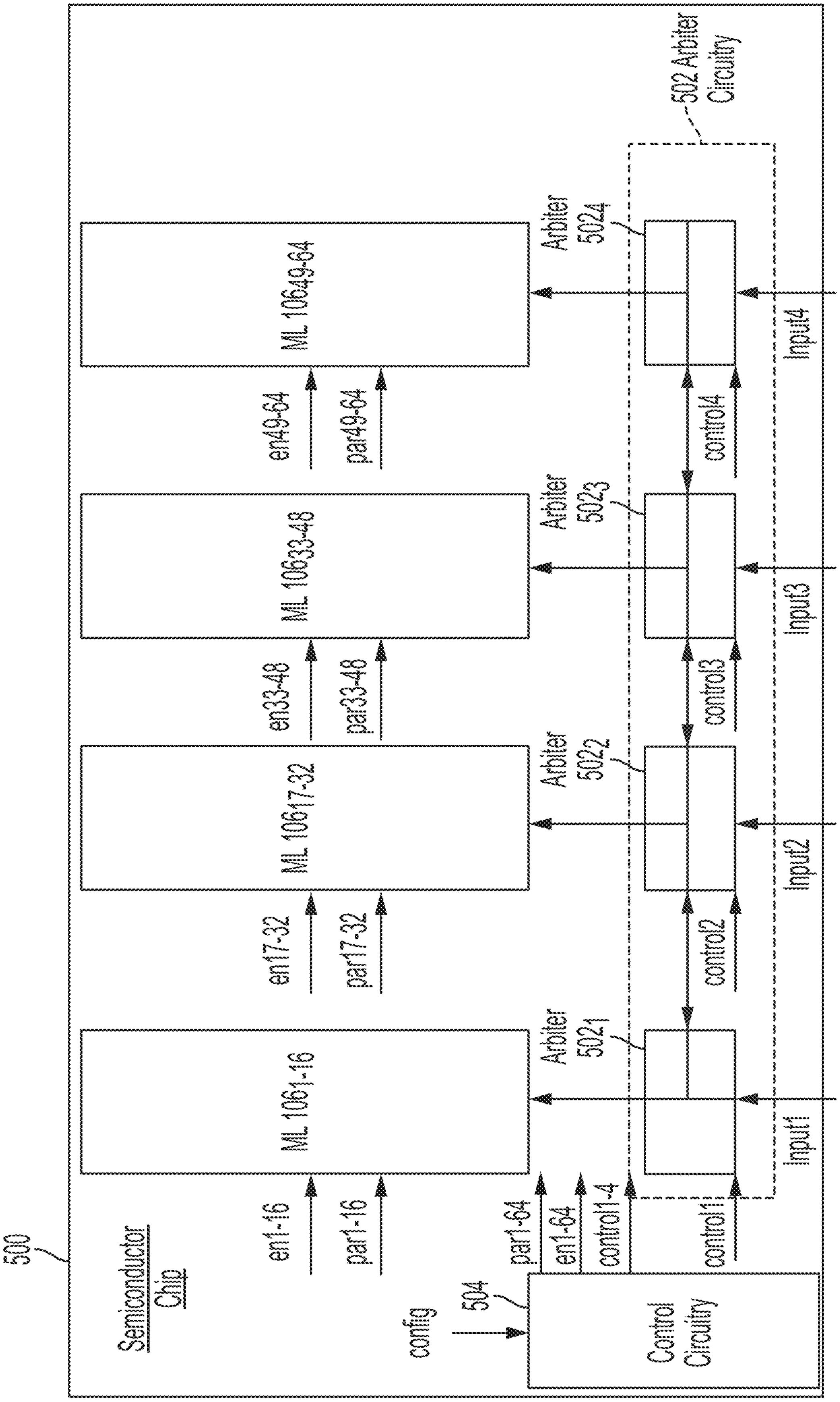
FIGS. 5A-5D, 6A-6B, and 7 illustrate schematic block diagrams of circuitry in an ultrasound device configured with different configurations, in accordance with certain embodiments described herein.
Figure 5B:
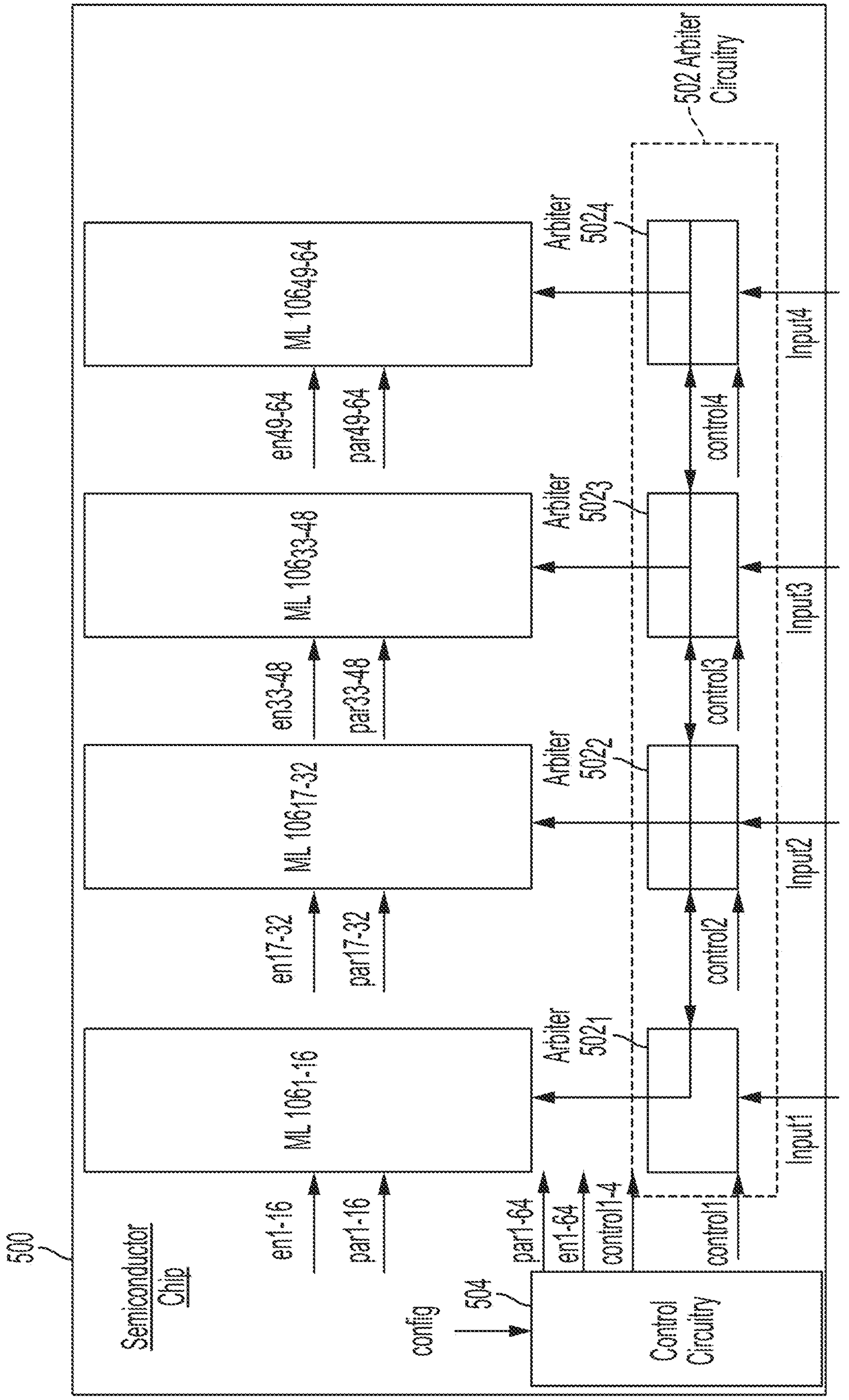
Figure 5C:
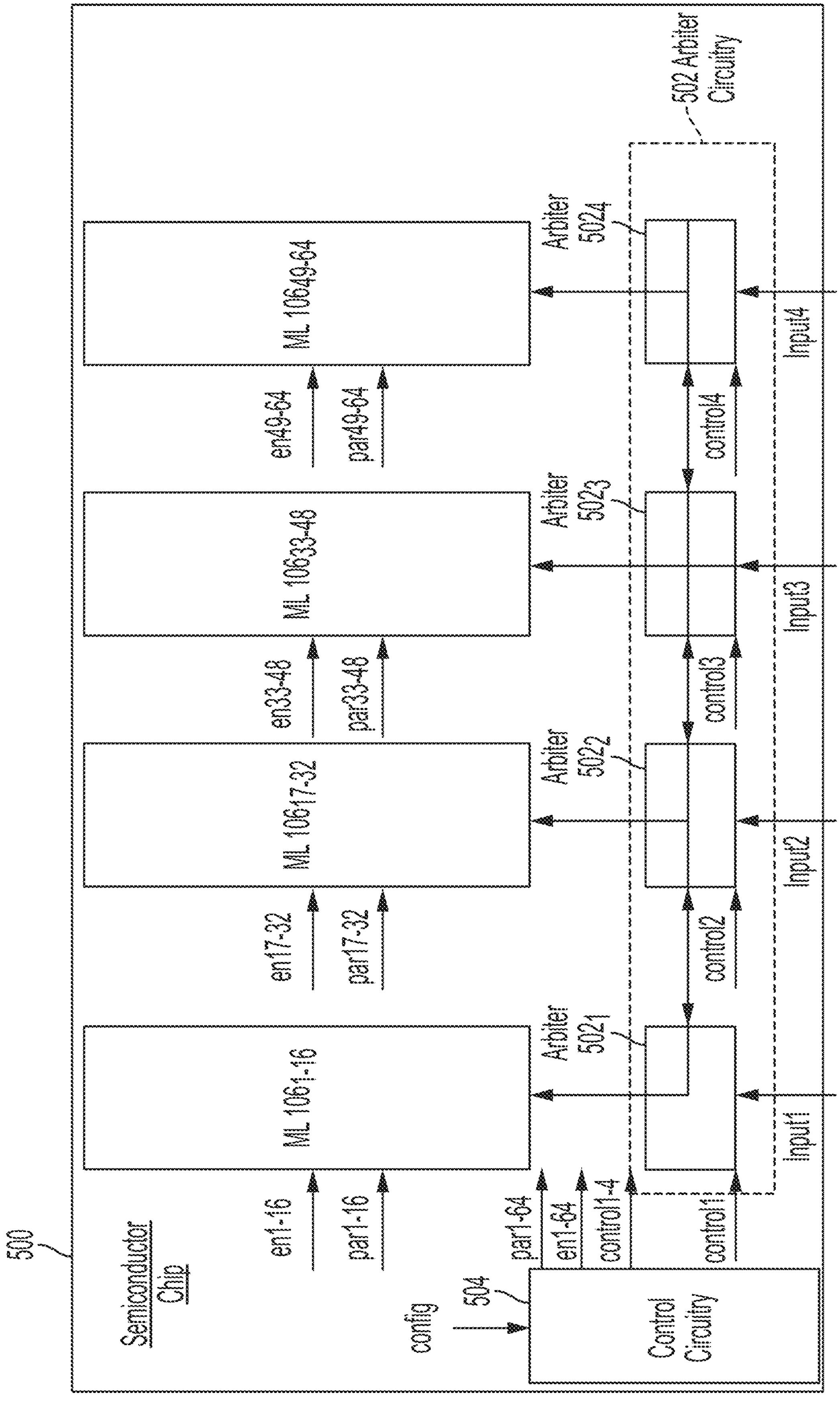
Figure 5D:
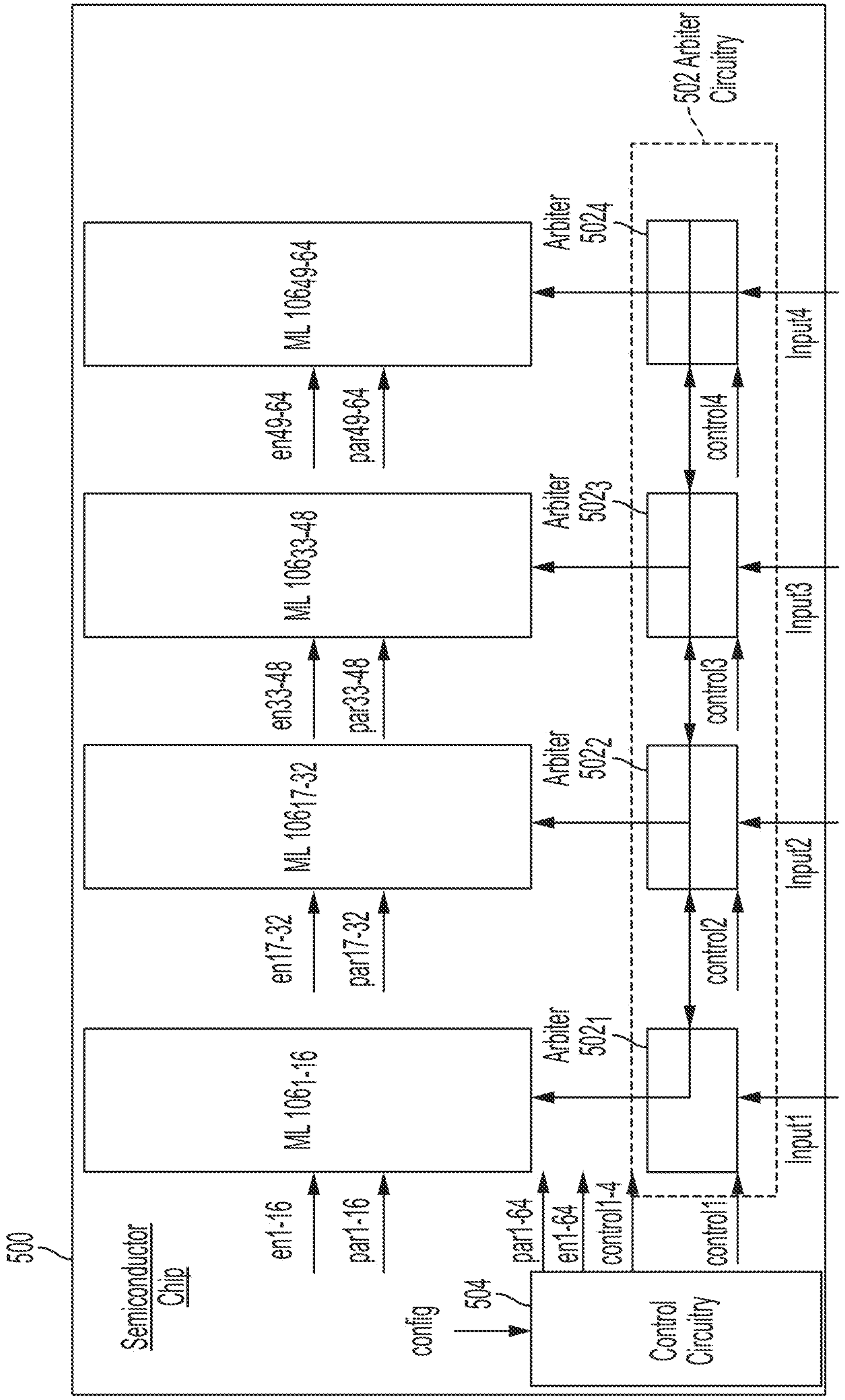

As illustrated in FIG. 5A, on a first processing cycle, the arbiter $\mathbf{502}_1$ may be configured to output the channel of ultrasound data $input_1$ (received from circuitry external to the arbiter circuitry 502 that is not illustrated) to the MLs $\mathbf{106}_{1-16}$ and to the arbiter $\mathbf{502}_2$. The arbiter $\mathbf{502}_2$ may be configured to output input (received from the arbiter $\mathbf{502}_1$) to the MLs $\mathbf{106}_{17-32}$ and to the arbiter $\mathbf{502}_3$. The arbiter $\mathbf{502}_3$ may be configured to output $input_1$ (received from the arbiter $\mathbf{502}_2$) to the MLs $\mathbf{106}_{33-48}$ and to the arbiter $\mathbf{502}_4$. The arbiter $\mathbf{502}_4$ may be configured to output input (received from the arbiter $\mathbf{502}_3$) to the MLs $\mathbf{106}_{49-64}$. Then as illustrated in FIG. 5B, on a subsequent processing cycle, the arbiter $\mathbf{502}_2$ may be configured to output the channel of ultrasound data $input_2$ (received from circuitry external to the arbiter circuitry 502 that is not illustrated) to the MLs $\mathbf{106}_{17-32}$ and to the arbiters $\mathbf{502}_1$ and $\mathbf{502}_3$. The arbiter $\mathbf{502}_3$ may be configured to output $input_2$ (received from the arbiter $\mathbf{502}_2$) to the MLs $\mathbf{106}_{33-48}$ and to the arbiter $\mathbf{502}_4$. The arbiter $\mathbf{502}_4$ may be configured to output $input_2$ (received from the arbiter $\mathbf{502}_3$) to the MLs $106_{49-64}$. The arbiter 502$_1$ may be configured to output input$_2$ (received from the arbiter 502$_2$) to the MLs 106$_{1-16}$. Then as illustrated in FIG. 5C, on a subsequent processing cycle, the arbiter 502$_3$ may be configured to output the channel of ultrasound data input$_3$ (received from circuitry external to the arbiter circuitry 502 that is not illustrated) to the MLs 106$_{33-48}$ and to the arbiters 502$_2$ and 502$_4$. The arbiter 502$_4$ may be configured to output input$_3$ (received from the arbiter 502$_3$) to the MLs 106$_{49-64}$. The arbiter 502$_2$ may be configured to output input$_3$ (received from the arbiter 502$_3$) to the MLs 106$_{17-32}$ and to the arbiter 502$_1$. The arbiter 502$_1$ may be configured to output input$_3$ (received from the arbiter 502$_2$) to the MLs 106$_{1-16}$. Then as illustrated in FIG. 5D, on a subsequent processing cycle, the arbiter 502$_4$ may be configured to output the channel of ultrasound data input$_4$ (received from circuitry external to the arbiter circuitry 502 that is not illustrated) to the MLs 106$_{49-64}$ and to the arbiter 502$_3$. The arbiter 502$_3$ may be configured to output input$_4$ (received from the arbiter 502$_4$) to the MLs 106$_{33-48}$ and to the arbiter 502$_2$. The arbiter 502$_2$ may be configured to output input$_4$ (received from the arbiter 502$_3$) to the MLs 106$_{17-32}$ and to the arbiter 502$_1$. The arbiter 502$_1$ may be configured to output input$_4$ (received from the arbiter 502$_2$) to the MLs 106$_{1-16}$.

It may thus take four processing cycles for the ultrasound device to process all four channels of ultrasound data, where processing the four channels of ultrasound data may include outputting 64 multilines per channel of ultrasound data. Because this configuration involves processing one channel of ultrasound data at a time by 64 MLs 106, this configuration may be referred to as a 1×64 configuration. The control circuitry 5004 may receive at config a particular configuration parameter specific to the 1×64 configuration, and based on this configuration parameter, output specific control signals at control$_{1-4}$ to cause the arbiters 502$_1$-502$_4$ to output one channel in parallel to the 64 MLs 106.

Only enabling a portion of the MLs 106 expands the possible configurations. Between 0 and 63 MLs 106 may be disabled. If k MLs 106 are enabled, because the configurations of FIGS. 5A-5D involve processing one channel of ultrasound data at a time by k MLs 106, these configurations may be referred to as 1×k configurations, where k may be between 1 and 64.

Figure 6A:
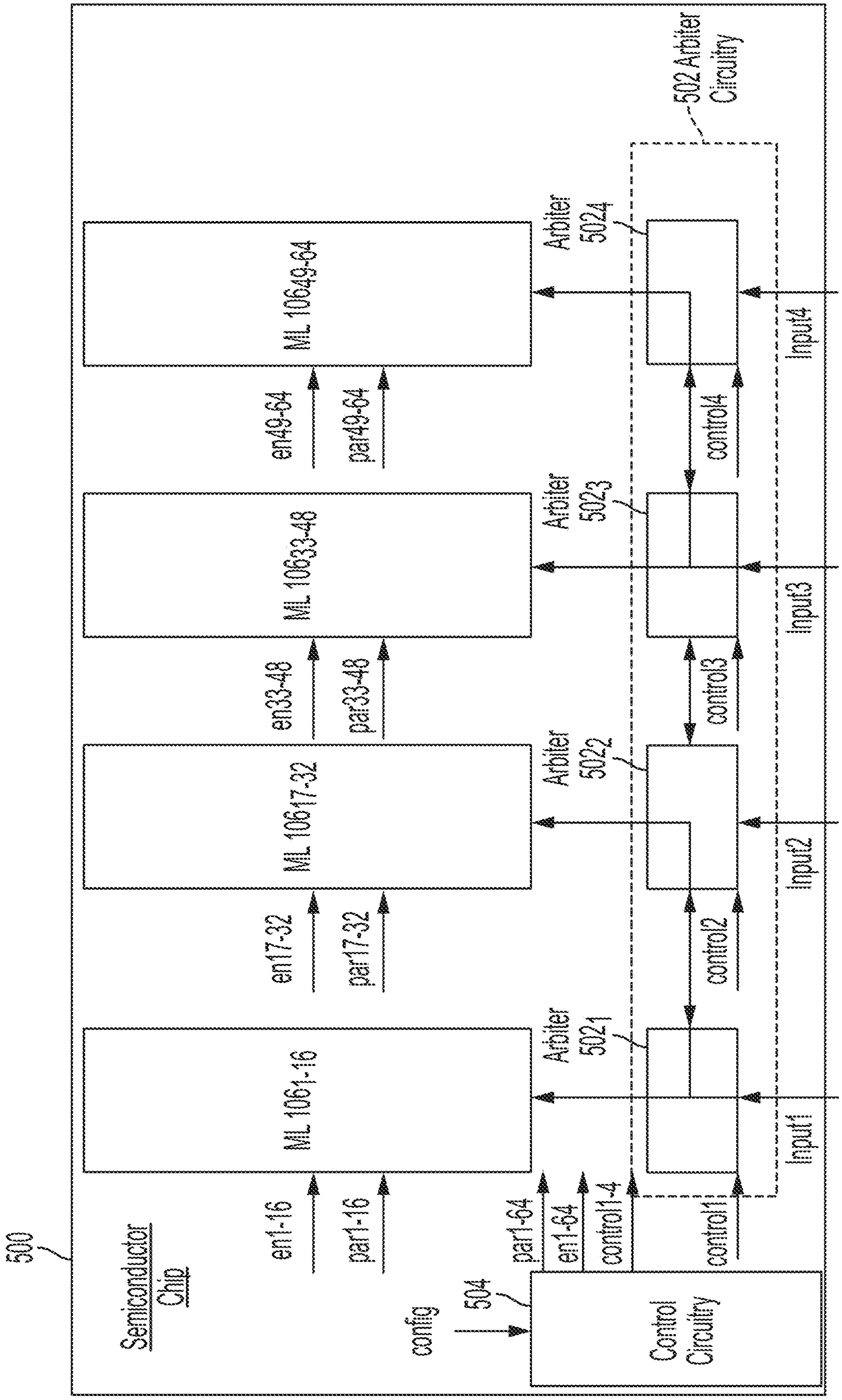
Figure 6B:
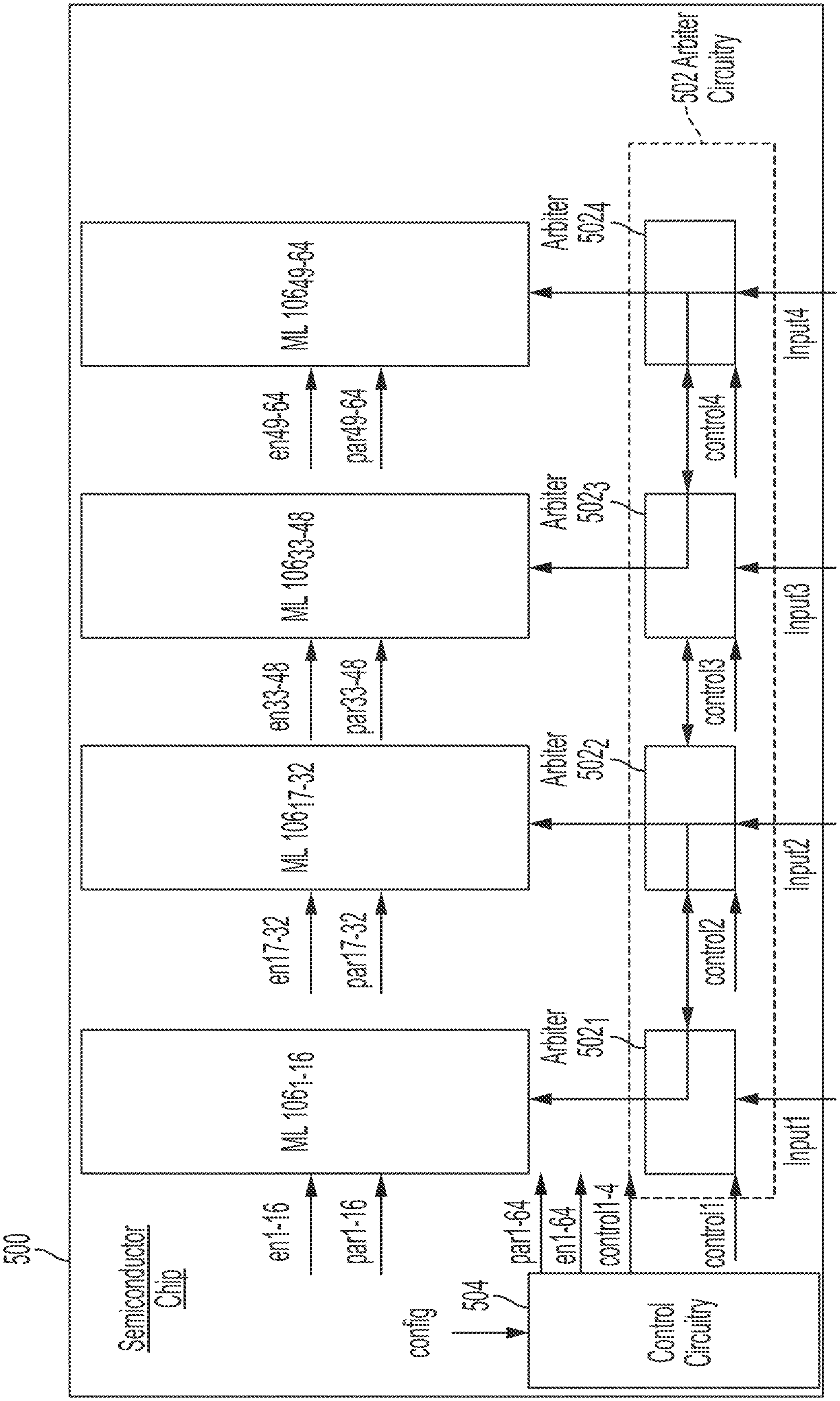

Referring to FIGS. 6A-6B, and assuming a configuration in which all the 64 MLs 106 are enabled, the arbiters 502$_1$-502$_2$ are configured to output one channel of ultrasound data to each of 32 MLs 106 and another channel of ultrasound data to each of the other 32 MLs 106 on each processing cycle. Thus, the 64 MLs 106 may be configured to together output 32 multilines per channel of ultrasound data. Each of the FIGS. 6A-6Bb illustrates a different processing cycle.

As illustrated in FIG. 6A, on a first processing cycle, the arbiter 502$_1$ may be configured to output the channel of ultrasound data input$_1$ (received from circuitry external to the arbiter circuitry 502 that is not illustrated) to the MLs 106$_{1-16}$ and to the arbiter 502$_2$. The arbiter 502$_2$ may be configured to output input (received from the arbiter 502$_1$) to the MLs 106$_{17-32}$. The arbiter 502$_3$ may be configured to output input$_3$ (received from circuitry external to the arbiter circuitry 502 that is not illustrated) to the MLs 106$_{33-48}$ and to the arbiter 502$_4$. The arbiter 502$_4$ may be configured to output input$_3$ (received from the arbiter 502$_3$) to the MLs 106$_{49-64}$. Then as illustrated in FIG. 6B, on a subsequent processing cycle, the arbiter 502$_2$ may be configured to output the channel of ultrasound data input$_2$ (received from circuitry external to the arbiter circuitry 502 that is not illustrated) to the MLs 106$_{17-32}$ and to the arbiter 502$_1$. The arbiter 502$_1$ may be configured to output input$_2$ (received from the arbiter 502$_2$) to the MLs 106$_{1-16}$. The arbiter 502$_4$ may be configured to output input$_4$ (received from circuitry external to the arbiter circuitry 502 that is not illustrated) to the MLs 106$_{49-64}$ and to the arbiter 502$_3$. The arbiter 502$_3$ may be configured to output input$_4$ (received from the arbiter 502$_4$) to the MLs 106$_{33-48}$.

The arbiters 502$_1$-502$_4$ may thus be configured to process two channels of ultrasound data in parallel, and it may thus take two processing cycles for the ultrasound device to process all four channels of ultrasound data, where processing the four channels of ultrasound data may include outputting 32 multilines per channel of ultrasound data. Because this configuration involves processing two channels of ultrasound data at a time by 32 MLs 106 each, this configuration may be referred to as a 2×32 configuration. The control circuitry 504 may receive at config a particular configuration parameter specific to the 2×32 configuration, and based on this configuration parameter, output specific control signals at control$_{1-4}$ to cause the arbiters 502$_1$-502$_4$ to output two channels in parallel to 32 MLs 106 each.

Only enabling a portion of the MLs 106 expands the possible configurations. Between 1 and 32 of $ML_{1-32}$ may be enabled and between 1 and 32 of $ML_{33-64}$ may be enabled. If k of $ML_{1-32}$ and k of $ML_{33-64}$ are enabled, because the configurations of FIGS. 6A-6B involve processing two channels of ultrasound data at a time by k MLs 106 each, these configurations may be referred to as a 2×k configurations, where k may be between 1 and 32.

Figure 7:
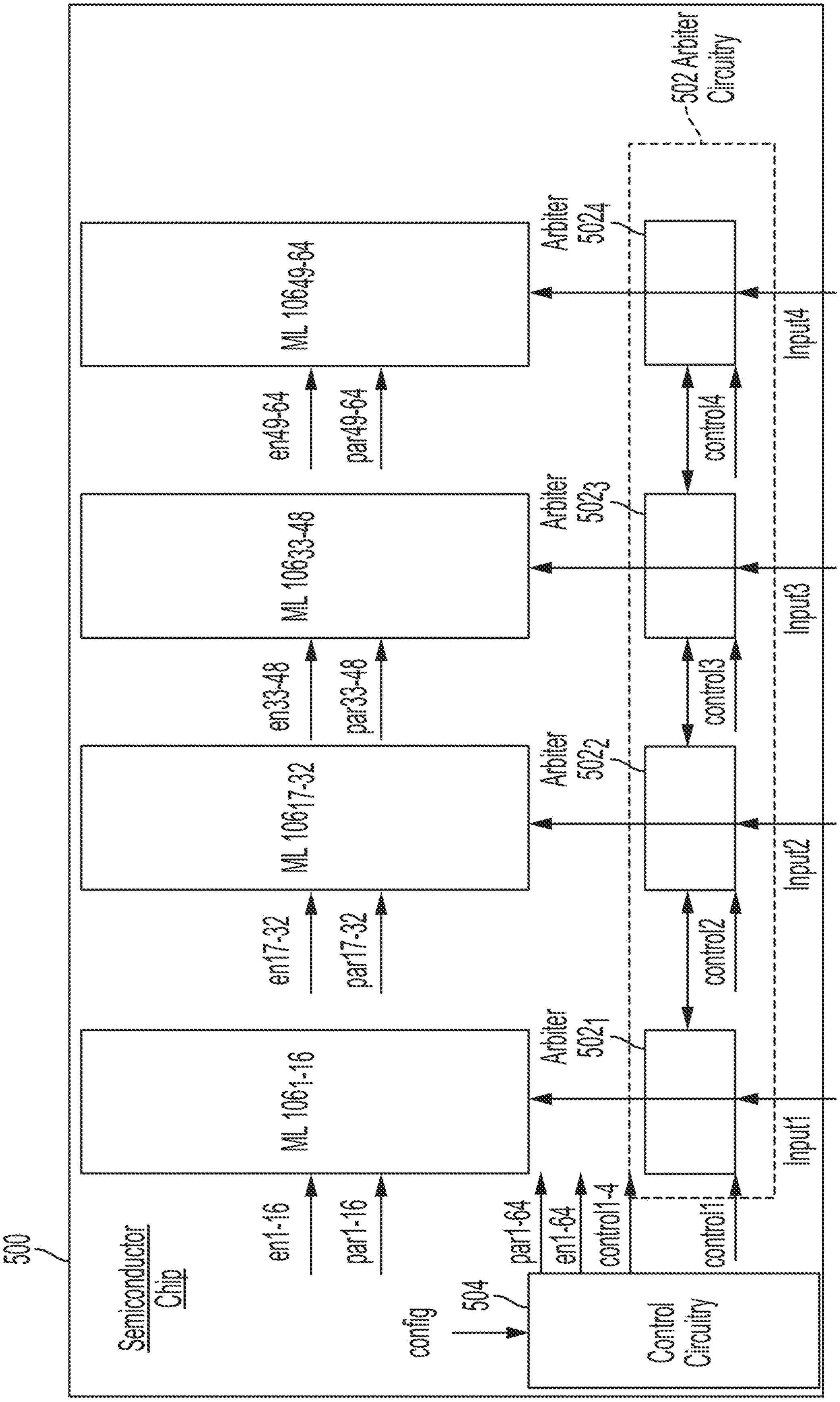

Referring to FIG. 7, and assuming that all 64 MLs 106 are enabled, the arbiters 502$_1$-502$_4$ are configured to output the channel of ultrasound data input to each of 16 MLs 106, another channel of ultrasound data to each of another 16 MLs 106, to output input$_2$ to each of another 16 MLs 106, to output input$_3$ to each of another 16 MLs 106, and to output input$_4$ to the other 16 MLs 106 on each processing cycle. Thus, the 64 MLs 106 may be configured to together output 16 multilines per channel of ultrasound data. On each processing cycle, the arbiter 502$_1$ may be configured to output input to the MLs 106$_{1-16}$, the arbiter 502$_2$ may be configured to output input$_2$ to the MLs 106$_{17-32}$, the arbiter 502$_3$ may be configured to output input$_3$ to the MLs 106$_{33-48}$, and the arbiter 502$_4$ may be configured to output input$_4$ to the MLs 106$_{49-64}$. The arbiters 502$_1$-502$_4$ may thus be configured to process four channels of ultrasound data in parallel, and it may thus take one processing cycle for the ultrasound device to process all four channels of ultrasound data, where processing the four channels of ultrasound data may include outputting 16 multilines per channel of ultrasound data. Because this configuration involves processing four channels of ultrasound data at a time by 16 MLs 106 each, this configuration may be referred to as a 4×16 configuration. The control circuitry 504 may receive at config a particular configuration parameter specific to the 4×16 configuration, and based on this configuration parameter, output specific control signals at control$_{1-4}$ to cause the arbiters 502$_1$-502$_4$ to output four channels in parallel to 16 MLs 106 each.

Only enabling a portion of the MLs 106 expands the possible configurations. Between 1 and 16 of $ML_{1-16}$ may be enabled, between 1 and 16 of $ML_{17-32}$ may be enabled, between 1 and 16 of $ML_{33-48}$ may be enabled, and between 1 and 16 of $ML_{49-64}$ may be enabled. If k of $ML_{1-16}$, k of $ML_{17-32}$, k of $ML_{33-48}$, and k of $ML_{49-64}$ are enabled, because the configurations of FIG. 7 involve processing four channels of ultrasound data at a time by k MLs 106 each, these configuration may be referred to as a 4×k configuration, where k may be between 1 and 16.

Figure 8:
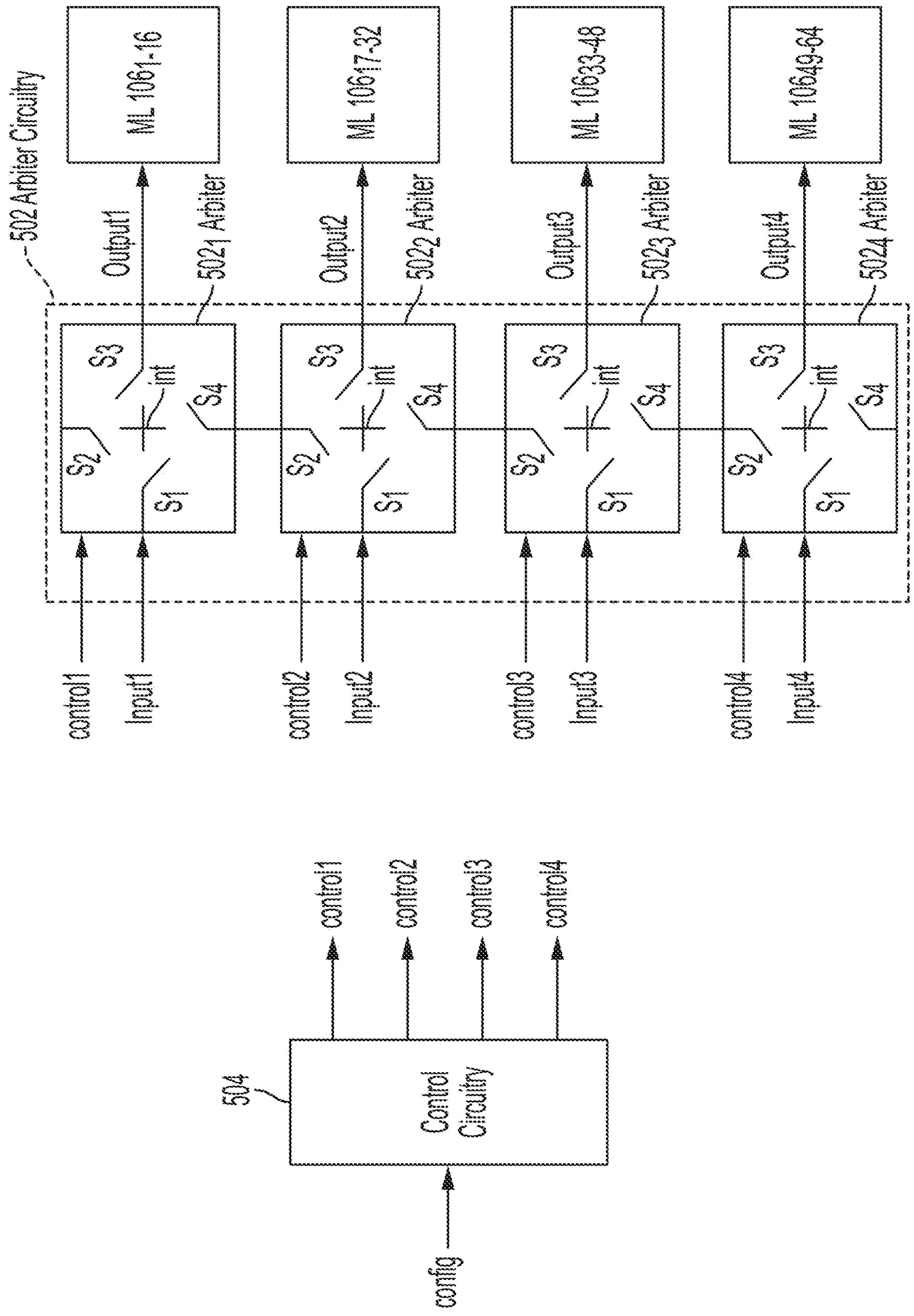
FIG. 8 illustrates the arbiters, the control circuitry, and the MLs of FIGS. 5A-7 in more detail.

FIG. 8 illustrates the arbiters 502$_1$-502$_4$, the control circuitry 504, and the MLs 106$_{1-64}$ in more detail. Each of the arbiters 502$_1$-502$_4$ includes four switches (referred to as $S_1$, $S_2$, $S_3$, and $S_4$) and an internal node int. Each switch $S_1$ is coupled between the internal node int and an input channel of ultrasound data (received from circuitry external to the arbiter circuitry 502 that is not illustrated). Each switch $S_3$ is coupled, at the output of a given arbiter 502, between the internal node int and certain MLs 106. The switches $S_2$ of the arbiters 502$_2$-502$_4$ are coupled between the internal node int and the switches $S_4$ of the arbiters 502$_1$-502$_3$, respectively. Based on which of the switches $S_1$, $S_2$, $S_3$, and $S_4$ are closed, a given arbiter 502 may be configured to route its input channel of ultrasound data to its output, to route its input channel of ultrasound data to an adjacent arbiter 502, to route a channel of ultrasound data received from an adjacent arbiter 502 to its output, and/or to route a channel of ultrasound data received from one adjacent arbiter 502 to another adjacent arbiter 502.

In operation, the control circuitry 504 may control which of the switches $S_1$, $S_2$, $S_3$, and $S_4$ in a given arbiter 502 are closed based on the control signals. Thus, for a 1×k configuration (i.e., one channel outputted at a time), the control circuitry 504 may output control signals such that each of the arbiters 502$_1$-502$_4$ outputs the same channel on a given processing cycle. For a 2×k configuration (i.e., two channels outputted in parallel at a time), the control circuitry 504 may output control signals such that two of the multiplexers (e.g., 502$_1$ and 502$_2$) output one channel and the other two multiplexers (502$_3$ and 502$_4$) output a different channel on a given processing cycle. For a 4×k configuration (i.e., four channels outputted in parallel at a time), the control circuitry 504 may output control signals such that each of the four arbiters 502$_1$-502$_4$ outputs a different channel on a given processing cycle. The control circuitry 504 may output particular control signals based on its received signal config, such that config controls the configuration. For example, if config has the value 00, then the control circuitry 504 may output control signals for a 1×k configuration. If config has the value 01, then the control circuitry 504 may output control signals for a 2×k configuration. If config has the value 10, then the control circuitry 504 may output control signals for a 4×k configuration. However, other schemes for config may be used instead. Table 2 illustrates in more detail which of the switches $S_1$, $S_2$, $S_3$, and $S_4$ in each of the arbiters 502$_1$-502$_4$ may be closed, based on the control signals, for different processing cycles in different configurations:

TABLE 2

Values of each of the control signals for different processing cycles in different configurations.

| Configuration | Processing Cycle | Switches closed in the arbiter $502_1$ (based on $control_1$) | Switches closed in the arbiter $502_2$ (based on $control_2$) | Switches closed in the arbiter $502_3$ (based on $control_3$) | Switches closed in the arbiter $502_4$ (based on $control_4$) | Outputs |
|---|---|---|---|---|---|---|
| 1 × k | 1 | $S_1$, $S_3$, $S_4$ | $S_2$, $S_3$, $S_4$ | $S_2$, $S_3$, $S_4$ | $S_2$, $S_3$ | $Output_{1,2,3,4} = Input_1$ |
| | 2 | $S_3$, $S_4$ | $S_1$, $S_2$, $S_3$, $S_4$ | $S_2$, $S_3$, $S_4$ | $S_2$, $S_3$ | $Output_{1,2,3,4} = Input_2$ |
| | 3 | $S_3$, $S_4$ | $S_2$, $S_3$, $S_4$ | $S_1$, $S_2$, $S_3$, $S_4$ | $S_2$, $S_3$ | $Output_{1,2,3,4} = Input_3$ |
| | 4 | $S_3$, $S_4$ | $S_2$, $S_3$, $S_4$ | $S_2$, $S_3$, $S_4$ | $S_1$, $S_2$, $S_3$ | $Output_{1,2,3,4} = Input4$ |
| 2 × k | 1 | $S_1$, $S_3$, $S_4$ | $S_2$, $S_3$ | $S_1$, $S_3$, $S_4$ | $S_2$, $S_3$ | $Output_{1,2} = Input_1$ $Output_{3,4} = Input_3$ |
| | 2 | $S_3$, $S_4$ | $S_1$, $S_2$, $S_3$ | $S_3$, $S_4$ | $S_1$, $S_2$, $S_3$ | $Output_{1,2} = Input_2$ $Output_{3,4} = Input_4$ |
| 4 × k | 1 | $S_1$, $S_3$ | $S_1$, $S_3$ | $S_1$, $S_3$ | $S_1$, $S_3$ | $Output_1 = Input_1$ $Output_2 = Input_2$ $Output_3 = Input_3$ $Output_4 = Input_4$ |

In some embodiments, each of the control signals may include multiple control signals controlling each switch in the corresponding arbiter 502. For example, consider that each of the switches in each arbiter 502 is a transmission gate having an N-type metal-oxide-semiconductor (nMOS) transistor and a P-type metal-oxide-semiconductor (pMOS) transistor. To close a given switch, a control signal may include a digital high voltage applied to the gate of the nMOS transistor and a digital low voltage applied to the gate of the pMOS transistor. To open a given switch, a control signal may include a digital low voltage applied to the gate of the nMOS transistor and a digital high voltage applied to the gate of the pMOS transistor. Different types of switches may use different types of control signals.

Generally, in arbiter circuitry of the type illustrated in FIG. 8, each of the arbiters may include a switch coupled between an internal node and a channel of ultrasound data received from circuitry external to the arbiter circuitry, a switch coupled between the internal node and the respective group of the multiple MLs, and at least one switch coupled between the internal node and another one of the multiple arbiters. Control circuitry may control, using control signals, which of the switches are closed and which are open. The control signals outputted by the control circuitry to each of the arbiters on a given processing cycle may be based on the configuration parameter config received by the control circuitry.

In any of the above description, in some embodiments, one processing cycle may include multiple clock cycles, and on each clock cycle, a different bit of each channel's data may be outputted from the arbiter circuitry 102 or from each of the arbiters $\mathbf{502}_1$-$\mathbf{502}_4$. Consider, for example, that each of $input_1$, $input_2$, $input_3$, and $input_4$ is s bits, and that the arbiter circuitry 102 is operating in a 1×k configuration. On clock cycle 1 of processing cycle 1, the arbiter circuitry 102 may output $input_1[0]$, on clock cycle 2 of processing cycle 1, the arbiter circuitry 102 may output $input_1[1]$, etc. On clock cycle s of processing cycle 1, the arbiter circuitry 102 may output $input_1[s-1]$. The subsequent clock cycle may be clock cycle 1 of processing cycle 2, and the arbiter circuitry 102 may output $input_2[0]$.

It should be appreciated that both the circuitry illustrated in FIGS. 1-4 and the circuitry illustrated in FIGS. 5-8 may enable the same functionality (e.g., the same configurations). However, the circuitry illustrated in FIGS. 1-4 may require more wires to be routed to the arbiter circuitry 102 than the circuitry illustrated in FIGS. 5-8 may require to be routed locally to each of the arbiters $\mathbf{502}_1$-$\mathbf{502}_4$. For example, if there are n input channels (where in the above examples, n=4) and each channel is s bits, then the arbiter circuitry 102 may require n×s wires to be routed to it. However, each of the arbiters $\mathbf{502}_1$-$\mathbf{502}_4$ may only require s wires to be routed to it. This may make physical layout of the circuitry illustrated in FIGS. 5-8 easier than physical layout of the circuitry illustrated in FIGS. 1-4.

It should be appreciated from the above description that different configurations of the ultrasound device may tradeoff on resolution and processing performance, where resolution may include the number of multilines the ultrasound device is configured to output per channel of ultrasound data, and processing performance many include how many channels of ultrasound data are processed per processing cycle. Generally, the above circuitry may enable switching from one configuration having a certain resolution and processing performance to a different configuration having either higher resolution and lower processing performance or lower resolution and higher processing performance. In some embodiments, the product of the processing performance and resolution may be constant for certain configurations. For example, considering just those configurations that do not include disabling certain MLs 106, namely the 1×64, 2×32, and 4×16 configurations, the product of the performance and resolution is 64 for all three configurations. Table 3 summarizes the resolution and processing performance for the example configurations described above.

TABLE 3

| Configuration | Processing Performance (Number of Input Channels Processed Per Processing cycle) | Resolution (Number of Multilines per input Channel) |
|---|---|---|
| 1 × 64 | 1 | 64 |
| 1 × 63 | 1 | 63 |
| 1 × 62 | 1 | 62 |
| . . . | . . . | . . . |
| 1 × 1 | 1 | 1 |
| 2 × 32 | 2 | 32 |
| 2 × 31 | 2 | 31 |
| 2 × 30 | 2 | 30 |
| . . . | . . . | . . . |
| 2 × 1 | 2 | 1 |
| 4 × 16 | 4 | 16 |
| 4 × 15 | 4 | 15 |
| 4 × 14 | 4 | 14 |
| . . . | . . . | . . . |
| 4 × 1 | 4 | 1 |

Resolution and performance for the configuration examples described above with reference to FIGs. 1A-8.

In the examples of FIGS. 1A-8, the arbiter circuitry 102 and the arbiters $\mathbf{502}_1$-$\mathbf{502}_4$ receive four channels of ultrasound data and there are 64 MLs 106, some of which may be disabled. However, it should be appreciated that the number of channels of ultrasound data received by the arbiter circuitry 102 and the arbiters $\mathbf{502}_1$-$\mathbf{502}_4$, and the number of MLs 106 illustrated in FIGS. 1A-8 are non-limiting, and other numbers may be used instead. As one specific example, the number of channels of ultrasound data received by the arbiter circuitry 102 and/or the arbiters $\mathbf{502}_1$-$\mathbf{502}_4$ may be 8. Generally, the circuitry may include one or more arbiters receiving n input channels of ultrasound data and configured to output all or some of these channels to m MLs 106 in parallel, where n, m, and m/n are integers. In some embodiments, the available configurations for this circuitry may be N×M (i.e., in a particular configuration, the arbiter outputs N channels in parallel, each to a group of M MLs), where N may be any integer from 1 to n and M may be any integer from 1 to m/n×floor (n/N). In some embodiments, only a subset of these configurations may be available. In the above examples of FIGS. 1A-8, n=4 and m=64.

In conventional ultrasound devices, the time it takes to process (e.g., to beamform) ultrasound data may be equal to the number of input channels of ultrasound data multiplied by the time required to process a single channel, regardless of the resolution used. In particular, even if the resolution is reduced (e.g., due to limited communication bandwidth over a communication link, such as a link between the ultrasound device and a processing device) by reducing the number of MLs that are used to process a single channel of ultrasound data, the time required to process the ultrasound data may not be reduced. In contrast, the circuitry and methods described above may allow for decreasing resolution while increasing performance (i.e., reducing processing time), or increasing resolution while decreasing performance (i.e., increasing processing time). In particular, as described above, control circuitry (e.g., the control circuitry 104 or 504) may control one or more arbiters (e.g., the arbiters 102 or 502$_1$-50$_4$) to increase the number of input channels processed on a single processing cycle and decrease how many MLs (e.g., the MLs 106) process each input channel (decreased resolution and increased performance). Using the N×M notation for configurations described above, this may correspond to a configuration with a high N and low M. Alternatively, the control circuitry may control the one or more arbiters to decrease the number of input channels processed on a single processing cycle and increase how many MLs process each input channel (increased resolution and decreased performance). Using the N×M notation for configurations described above, this may correspond to a configuration with a low N and high M. Thus, for applications where it may be desirable to reduce processing time, such as for imaging of the heart where it may be desirable to capture multiple ultrasound images during a single heartbeat, processing time may be reduced by reducing resolution. This may correspond to configurations with high N and low M. On the other hand, for applications where high resolution may be desirable and reduced processing time may not be critical, such as for imaging of the abdomen where there may be a large field-of-view, resolution may be increased by increasing processing time. This may correspond to configurations with low N and high M.

Figure 9:
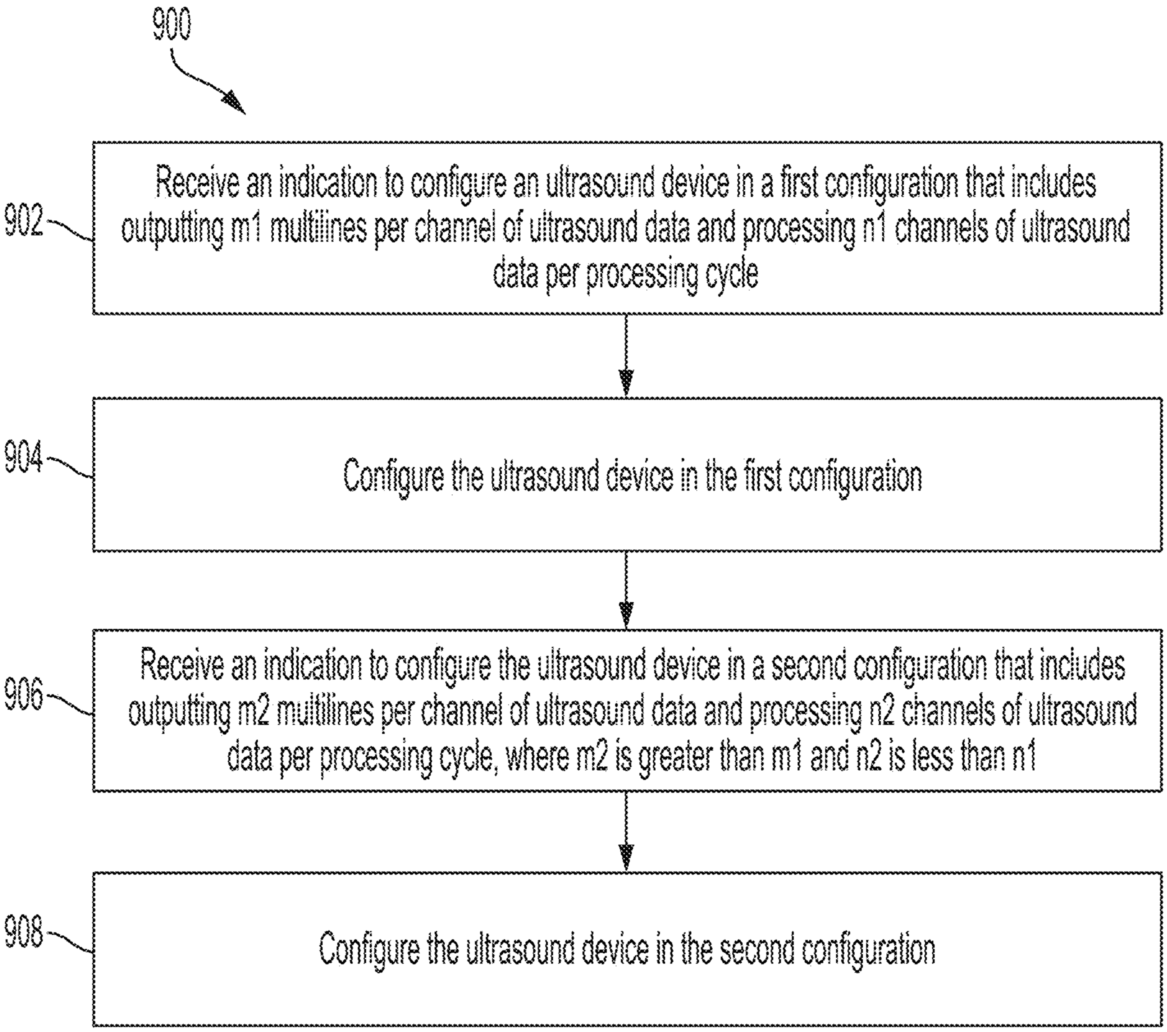
FIGS. 9 and 10 illustrate a flow diagram of respective processes for configuring circuitry in an ultrasound device, in accordance with certain embodiments described herein.
Figure 10:
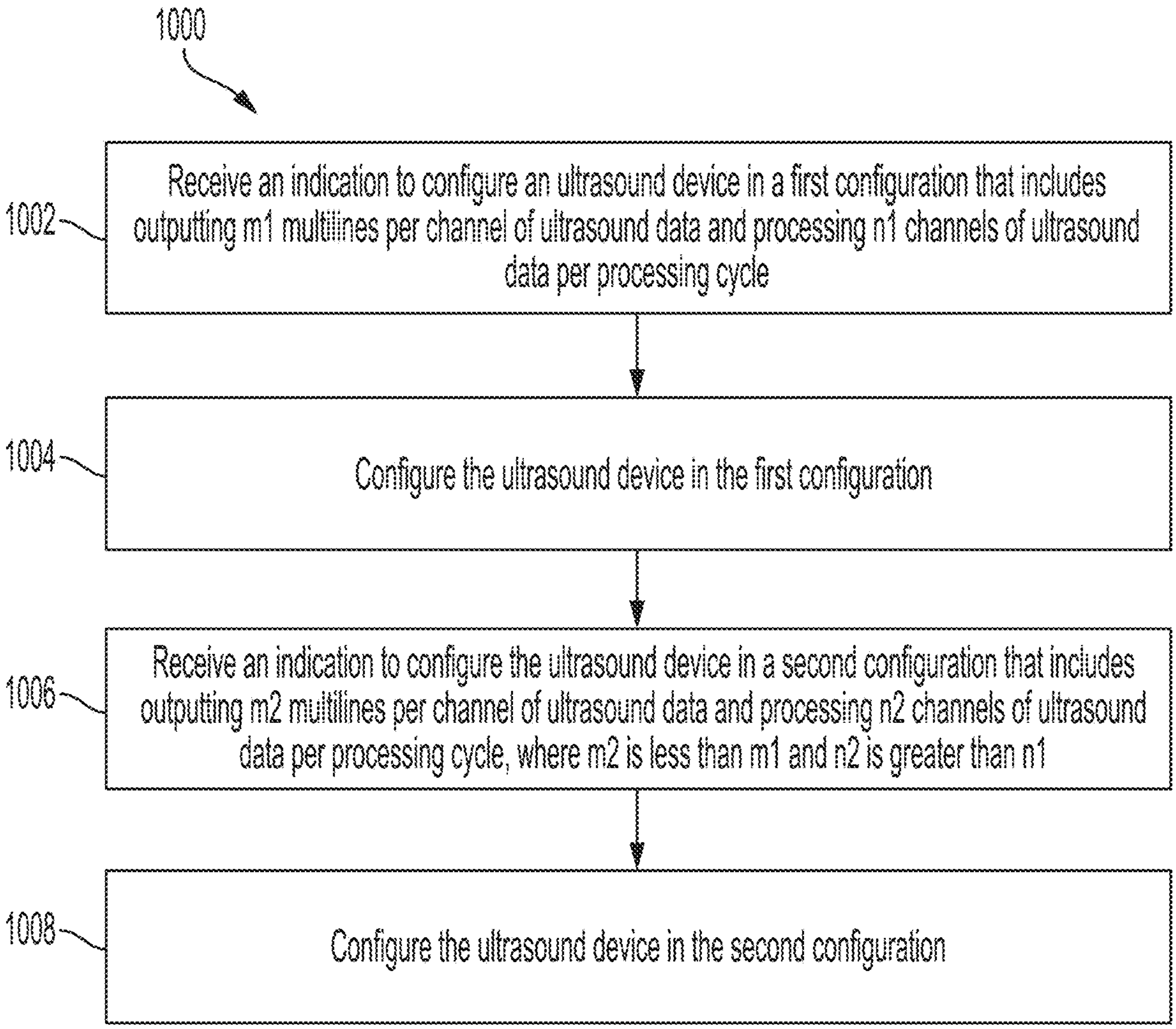

FIGS. 9 and 10 illustrate a flow diagram of processes 900 and 1000, respectively, for configuring circuitry in an ultrasound device, in accordance with certain embodiments described herein. In some embodiments, the processes 900 and 1000 may be performed using control circuitry (e.g., the control circuitry 104 or 504) that is configured to perform each of the acts of the processes 900 and 1000. In some embodiments, a processing device (e.g., a smartphone, tablet, or laptop) may be in operative communication with the ultrasound device. The processing device and the ultrasound device may communicate over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link. The processing device may be configured to transmit control signals to the control circuitry in the ultrasound device over the communication link to control the configuration. The circuitry in the ultrasound device described with reference to the processes 900 and 1000 may be integrated in a semiconductor chip (e.g., the semiconductor chips 100 or 500, or in some embodiments, in multiple semiconductor chips) in the ultrasound device. In the following description of the processes 900 and 1000, n and m (which may include subscripts) are all integer numbers.

Generally, the processes 900 and 1000 include configuring the ultrasound device to output a certain number of multilines per channel of ultrasound data and process a certain channels of ultrasound data per processing cycle, and then configuring the ultrasound device to either output more multilines per channel (increased resolution) and process fewer channels per processing cycle (decreased processing performance), or output fewer multilines per channel (decreased resolution) and process more channels per processing cycle (increased processing performance). The ultrasound device may be capable of both changing to a configuration that involves outputting more multilines per channel and processing fewer channels per processing cycle and to a configuration that involves outputting fewer multilines per channels and processing more channels per processing cycle.

Each of the channels of ultrasound data may be received from other circuitry; for example, each may be the output of an analog-to-digital converter (ADC) configured to convert analog ultrasound data from one or more particular ultrasound transducers in the ultrasound device, the output of an ultrasound processing unit (UPU) in the ultrasound device that may include one or more such ADCs, or the output of any other group of circuitry in the ultrasound device.

The ultrasound device may include multiline processing units (MLs, e.g., the MLs 106), which may be circuitry configured to receive a channel of ultrasound data as an input and project that channel's ultrasound data onto a particular portion of an ultrasound image (where the particular portion of the ultrasound image may be referred to as a multiline). The ultrasound device (or a processing device receiving data from the ultrasound device) may be configured to use the outputs of all the MLs together to form an output ultrasound image. The $m_1$ multilines outputted per channel of ultrasound data may be equivalent to the number of MLs receiving a given channel of ultrasound data on a given processing cycle. With each processing cycle, a different channel of ultrasound data may be outputted to each of the $m_1$ MLs, until all the channels of ultrasound data have been processed after $n_1$ processing cycles. As a specific example, consider that there are four channels of ultrasound data to be processed and 64 available MLs (e.g., as in the circuitry illustrated in FIGS. 1A-8). This configuration may include the circuitry in the ultrasound device being configured to process each of these channels by $m_1$=32 MLs on each processing cycle, with $n_1$=2 channels processed per processing cycle, such that processing all four channels may require two processing cycles. This may be referred to as 2×32 configuration.

The process 900 includes configuring the ultrasound device in a first configuration that includes outputting a certain number of multilines per channel of ultrasound data and processing a certain channels of ultrasound data per processing cycle, and then configuring the ultrasound device in a second configuration that includes outputting more multilines per channel (increased resolution) and process fewer channels per processing cycle (decreased processing performance). As non-limiting examples, the first configuration may be a 2×32 configuration and the second configuration may be a 1×64 configuration, or the first configuration may be a 4×16 configuration and the second configuration may be a 2×32 configuration, or the first configuration may be a 4×16 configuration and the second configuration may be a 1×64 configuration.

The process 900 begins at act 902. In act 902, an indication is received to configure the ultrasound device in a first configuration that includes outputting $m_1$ multilines per channel of ultrasound data and processing $n_1$ channels of ultrasound data per processing cycle. The indication may be based, for example, on the user selecting (e.g., from a menu displayed by the processing device) to image a particular anatomy, or based on an automatic selection (e.g., by the processing device) to image a particular anatomy (e.g., as a part of an automatic workflow), where the particular anatomy may be associated with the first configuration. The processing device may transmit a command to the ultrasound device, which may supply a configuration parameter (e.g., the config signal described above) specific to the first configuration to the control circuitry in the ultrasound device. In some embodiments, the ultrasound device may automatically select to image a particular anatomy (e.g., as a part of an automatic workflow), where the particular anatomy may be associated with the first configuration. The ultrasound device may supply a configuration parameter (e.g., the config signal described above) specific to the first configuration to the control circuitry in the ultrasound device. The configuration parameter may be the indication. The process 900 proceeds from act 902 to act 904.

In act 904, the ultrasound device is configured in the first configuration. Control circuitry (e.g., the control circuitry 104 or the control circuitry 504) and arbiter circuitry (e.g., the arbiter circuitry 102 or the arbiter circuitry 502) may facilitate configuration of the circuitry in the ultrasound device in the first configuration. Further description of how arbiter circuitry may configure an ultrasound device in different configurations may be found with reference to FIGS. 1A-8. The process 900 proceeds from act 904 to acct 906.

In act 906, an indication is received to configure the ultrasound device in a second configuration that includes outputting $m_2$ multilines per channel of ultrasound data and processing $n_2$ channels of ultrasound data per processing cycle, where $m_2$ is greater than $m_1$ and $n_2$ is less than $n_1$. In other words, in the second configuration the number of multilines outputted per channel of ultrasound data is greater than in the first configuration, but the number of channels of ultrasound data processed per processing cycle is less than in the first configuration. As specific non-limiting examples of n1 and n2, n1 may be 2 and n2 may be 1, n1 may be 4 and n2 may be 2, n1 may be 4 and n2 may be 1, n1 may be 8 and n2 may be 4, n1 may be 8 and n2 may be 2, or n1 may be 8 and n2 may be 1.

As in act 902, the indication at act 906 may be based, for example, on the user selecting (e.g., from a menu displayed by the processing device) to change to image a different anatomy, or based on an automatic selection (e.g., by the processing device) to change to image a different anatomy (e.g., as a part of an automatic workflow), where the different anatomy may be associated with the second configuration, different from the first configuration. The processing device may transmit a command to the ultrasound device, which may supply a configuration parameter (e.g., the config signal described above) specific to the second configuration to the control circuitry in the ultrasound device. In some embodiments, the ultrasound device may automatically select to image a different anatomy (e.g., as a part of an automatic workflow), where the different anatomy may be associated with the second configuration, different from the first configuration. The ultrasound device may supply a configuration parameter (e.g., the config signal described above) specific to the second configuration to the control circuitry in the ultrasound device. The configuration parameter may be the indication. The process 900 proceeds from act 906 to act 908.

In act 908, the ultrasound device is configured in the second configuration. As described with reference to act 904, control circuitry (e.g., the control circuitry 104 or the control circuitry 504) and arbiter circuitry (e.g., the arbiter circuitry 102 or the arbiter circuitry 502) may facilitate configuration of the circuitry in the ultrasound device in the second configuration. Further description of how arbiter circuitry may configure an ultrasound device in different configurations may be found with reference to FIGS. 1A-8. As particular examples for the process 900, for applications where it may be desirable to reduce processing time, such as for imaging of the heart where it may be desirable to capture multiple ultrasound images during a single heartbeat, processing time may be reduced (i.e., performance may be increased) by reducing resolution. Using the N×M notation for configurations described above, this may correspond to a configuration with a high N and low M. On the other hand, for applications where high resolution may be desirable and reduced processing time may not be critical, such as for imaging of the abdomen where there may be a large field-of-view, resolution may be increased by increasing processing time (i.e., reducing performance). This may correspond to configurations with low N and high M. Thus, if the ultrasound device is configured in a first configuration for imaging the heart at act 904, and a selection is made to change to imaging the abdomen at act 906, in act 908 the ultrasound device may be configured in a second configuration for imaging the abdomen that includes increased resolution and decreased performance. Using these examples anatomies and the example configurations described above, the heart may be associated with the 2×32 configuration and the abdomen may be associated with the 1×64 configuration. However, these examples are non-limiting, and these anatomies may be associated with other configurations. As further specific non-limiting examples, the heart may be associated with the 4×16 configuration and the abdomen may be associated with the 2×32 configuration, or the heart may be associated with the 4×16 configuration and the abdomen may be associated with the 1×64 configuration.

The process 1000 includes configuring the ultrasound device in a first configuration that includes outputting a certain number of multilines per channel of ultrasound data and processing a certain channels of ultrasound data per processing cycle, and then configuring the ultrasound device in a second configuration that includes outputting fewer multilines per channel (decreased resolution) and processing more channels per processing cycle (increased processing performance). As non-limiting examples, the first configuration may be a 2×32 configuration and the second configuration may be a 4×16 configuration, or the first configuration may be a 1×64 configuration and the second configuration may be a 2×32 configuration, or the first configuration may be a 1×64 configuration and the second configuration may be a 4×16 configuration.

The process 1000 begins at act 1002. In act 1002, an indication is received to configure the ultrasound device in a first configuration that includes outputting $m_1$ multilines per channel of ultrasound data and processing $n_1$ channels of ultrasound data per processing cycle. The indication may be based, for example, on the user selecting (e.g., from a menu displayed by the processing device) to image a particular anatomy, or based on an automatic selection (e.g., by the processing device) to image a particular anatomy (e.g., as a part of an automatic workflow), where the particular anatomy may be associated with the first configuration. The processing device may transmit a command to the ultrasound device, which may supply a configuration parameter (e.g., the config signal described above) specific to the first configuration to the control circuitry in the ultrasound device. In some embodiments, the ultrasound device may automatically select to image a particular anatomy (e.g., as a part of an automatic workflow), where the particular anatomy may be associated with the first configuration. The ultrasound device may supply a configuration parameter (e.g., the config signal described above) specific to the first configuration to the control circuitry in the ultrasound device. The configuration parameter may be the indication. The process 1000 proceeds from act 1002 to act 1004.

In act 1004, the ultrasound device is configured in the first configuration. Control circuitry (e.g., the control circuitry 104 or the control circuitry 504) and arbiter circuitry (e.g., the arbiter circuitry 102 or the arbiter circuitry 502) may facilitate configuration of the circuitry in the ultrasound device in the first configuration. Further description of how arbiter circuitry may configure an ultrasound device in different configurations may be found with reference to FIGS. 1A-8. The process 900 proceeds from act 1004 to act 1006.

In act 1006, an indication is received to configure the ultrasound device in a second configuration that includes outputting $m_2$ multilines per channel of ultrasound data and processing $n_2$ channels of ultrasound data per processing cycle, where $m_2$ is less than $m_1$ and $n_2$ is greater than $n_1$. In other words, in the second configuration the number of multilines outputted per channel of ultrasound data is less than in the first configuration, but the number of channels of ultrasound data processed per processing cycle is greater than in the first configuration. As specific non-limiting examples, n1 may be 1 and n2 may be 2, n1 may be 2 and n2 may be 4, n1 may be 1 and n2 may be 4, n1 may be 4 and n2 may be 8, n1 may be 2 and n2 may be 8, or n1 may be 1 and n2 may be 8.

As in act 1002, the indication at act 1006 may be based, for example, on the user selecting (e.g., from a menu displayed by the processing device) to change to image a different anatomy, or based on an automatic selection (e.g., by the processing device) to change to image a different anatomy (e.g., as a part of an automatic workflow), where the different anatomy may be associated with the second configuration, different from the first configuration. The processing device may transmit a command to the ultrasound device, which may supply a configuration parameter (e.g., the config signal described above) specific to the second configuration to the control circuitry in the ultrasound device. In some embodiments, the ultrasound device may automatically select to image a different anatomy (e.g., as a part of an automatic workflow), where the different anatomy may be associated with the second configuration, different from the first configuration. The ultrasound device may supply a configuration parameter (e.g., the config signal described above) specific to the second configuration to the control circuitry in the ultrasound device. The configuration parameter may be the indication.

In act 1008, the ultrasound device is configured in the second configuration. As described with reference to act 1004, control circuitry (e.g., the control circuitry 104 or the control circuitry 504) and arbiter circuitry (e.g., the arbiter circuitry 102 or the arbiter circuitry 502) may facilitate configuration of the circuitry in the ultrasound device in the second configuration. Further description of how arbiter circuitry may configure an ultrasound device in different configurations may be found with reference to FIGS. 1A-8.

As particular examples for the process 1000, for applications where it may be desirable to reduce processing time, such as for imaging of the heart where it may be desirable to capture multiple ultrasound images during a single heartbeat, processing time may be reduced (i.e., performance may be increased) by reducing resolution. Using the N×M notation for configurations described above, this may correspond to a configuration with a high N and low M. On the other hand, for applications where high resolution may be desirable and reduced processing time may not be critical, such as for imaging of the abdomen where there may be a large field-of-view, resolution may be increased by increasing processing time (i.e., reducing performance). This may correspond to configurations with low N and high M. Thus, if the ultrasound device is configured in a first configuration for imaging the abdomen at act 1004, and a selection is made to change to imaging the heart at act 1006, in act 1008 the ultrasound device may be configured in a second configuration for imaging the heart that includes increased performance and decreased resolution. Using these examples anatomies and the example configurations described above, the abdomen may be associated with the 1×64 configuration and the heart may be associated with the 2×32 configuration. However, these examples are non-limiting, and these anatomies may be associated with other configurations. As further specific non-limiting examples, the abdomen may be associated with the 2×32 configuration and the heart may be associated with the 4×16 configuration, or the abdomen may be associated with the 1×64 configuration and the heart may be associated with the 4×16 configuration.

As described above, the ultrasound device may be capable of performing both the process 900 and the process 1000. Consider that the ultrasound device is configured in a particular configuration that includes outputting a certain number of multilines per channel of ultrasound data and processing a certain channels of ultrasound data per processing cycle. If the ultrasound device receives an indication to change to a configuration that includes outputting more multilines per channel and processing fewer channels per processing cycle, then the ultrasound device may do so (the process 900). If the ultrasound device receives an indication to change to a different configuration that includes outputting fewer multilines per channel and processing more channels per processing cycle, then the ultrasound device may do so (the process 1000).

In some embodiments, acts 902 and 904 and/or acts 1002 and 1004 may be absent, such as if the ultrasound device is configured in the first configuration by default.

In some embodiments, the MLs 106 may be implemented as discrete groups. In some embodiments, the number of groups may be the same as the number of input channels received by the arbiter (e.g., the arbiter circuitry 102) or arbiters (e.g., the arbiters $\mathbf{502}_1$-$\mathbf{502}_4$). In the examples of FIGS. 1A-8, the number of input channels is 4, and thus there are 4 groups of MLs 106, namely MLs $\mathbf{106}_{1\text{-}16}$, MLS $\mathbf{106}_{17\text{-}32}$, MLS $\mathbf{106}_{33\text{-}48}$, MLS $\mathbf{106}_{49\text{-}64}$. In embodiments with the same number of input channels to the arbiter(s) but different total number of MLs 106, the number of MLs 106 per group may be different.

Figure 11:
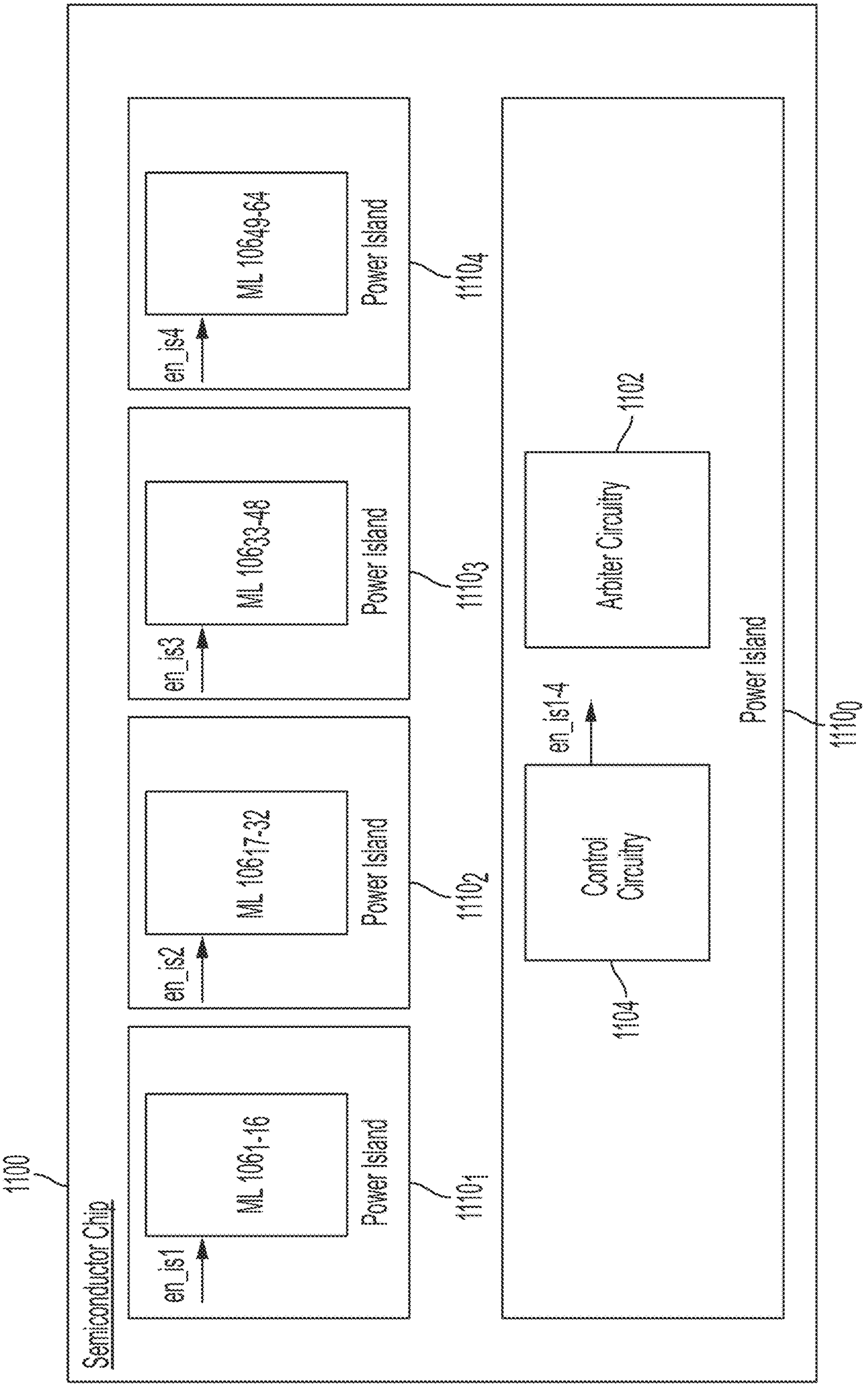
FIG. 11 illustrates a schematic block diagram of circuitry in an ultrasound device, in accordance with certain embodiments described herein.

The inventors have recognized that it may be helpful to completely disable one or more groups of MLs 106 in order to reduce those group(s) power consumption to zero and generally reduce power consumption of the ultrasound device. The inventors have recognized that implementing different power islands for each group of MLs 106 may be helpful. A power island may be a group of circuitry whose power may be controlled independently from the rest of a device, and hence may be completely powered down while not powering down circuitry in other power islands. FIG. 11 illustrates a schematic block diagram of circuitry in an ultrasound device, in accordance with certain embodiments described herein. FIG. 11 includes a semiconductor chip 1100, arbiter circuitry 1102, control circuitry 1104, the MLs 106, and power islands $\mathbf{1110}_{0\text{-}4}$. The circuitry illustrated in FIG. 11 may be the same as the circuitry illustrated in FIGS. 1A-8. Thus, the semiconductor chip 1100 may be the same as the semiconductor chip 100 and/or 500, the arbiter circuitry 1102 may be the same as the arbiter circuitry 102 and/or the arbiter circuitry 502, and the control circuitry 1104 may be the same as the control circuitry 104 and/or 504. Various control signals and couplings between various circuits that are described above are omitted from FIG. 11 for simplicity.

In FIG. 11, each group of MLs 106 (where the four groups of MLs 106 are MLs $\mathbf{106}_{1\text{-}16}$, MLs $\mathbf{106}_{17\text{-}32}$, MLs $\mathbf{106}_{33\text{-}48}$, MLs $\mathbf{106}_{49\text{-}64}$) is implemented in a different power island. The MLs $\mathbf{106}_{1\text{-}16}$ are in the power island $\mathbf{1110}_1$, the MLs $\mathbf{106}_{17\text{-}32}$ are in the power island $\mathbf{1110}_2$, the MLs $\mathbf{106}_{33\text{-}48}$ are in the power island $\mathbf{1110}_3$, and the MLs $\mathbf{106}_{49\text{-}64}$ are in the power island $\mathbf{1110}_4$. Additionally, the control circuitry 1104 and the arbiter circuitry 1102 are in a separate power island, the power island $\mathbf{1110}_0$. The power consumed by a group of MLs 106 may be reduced to zero by disabling the corresponding power island 1110. FIG. 11 further illustrates how the control circuitry 1104 outputs enable signals $en\_is_{1\text{-}4}$, one to each of the power islands $\mathbf{1110}_{1\text{-}4}$. The control circuitry 1104 may use each of the enable signals $en\_is_{1\text{-}4}$ to disable the corresponding power island 1110.

While the above description has described circuitry (e.g., MLs, arbiter(s), and control circuitry) integrated on a semiconductor chip or one or more semiconductor chips, in some embodiments such circuitry may be implemented in other devices, such as in a field-programmable gate array (FPGA).

It should be appreciated that the methods and circuitry described in this application may be used for any beamforming algorithm employed by the MLs 106.

It should also be appreciated that the flexibility afforded by the different configurations described herein, as well as the low-power operation options described herein (e.g., through the use of power islands) may be especially helpful for low-power and/or wearable ultrasound devices, although this application is not limited to low-power and/or wearable ultrasound devices (e.g., ultrasound patches), and any type of ultrasound device may use the methods and circuitry described herein.

According to an aspect of the present application, an ultrasound device is provided, comprising arbiter circuitry configured to receive multiple channels of ultrasound data; multiline processing units (MLs) configured to process channels of ultrasound data to produce multilines; and control circuitry configured to control which of the multiple channels of ultrasound data the arbiter circuitry outputs to which of the MLs on which processing cycle.

In some embodiments, the control circuitry, the arbiter circuitry, and the MLs are integrated in a semiconductor chip.

In some embodiments, the ultrasound device of claim B7, wherein the semiconductor chip further comprises multiple power islands, the MLs comprise multiple groups of MLs, and each of the multiple groups of MLs is implemented in a different one of the multiple power islands.

In some embodiments, a number of the multiple groups of MLs is equal to a number of the multiple ultrasound data channels.

According to an aspect of the present application, an ultrasound device is provided, comprising control circuitry, multiline processing units (MLs) configured to process channels of ultrasound data to produce multilines, and arbiter circuitry comprising multiplexers, wherein each of the multiplexers comprises multiple input terminals each coupled to one of multiple channels of ultrasound data, a control terminal coupled to the control circuitry, and an output terminal coupled to a group of the MLs.

According to an aspect of the present application, an ultrasound device is provided, comprising control circuitry, multiline processing units (MLS) configured to process channels of ultrasound data to produce multilines, and arbiter circuitry comprising arbiters, wherein each of the arbiters comprises an internal node, a switch controlled by the control circuitry and coupled between the internal node and one of multiple channels of ultrasound data, a switch controlled by the control circuitry and coupled between the internal node and a group of the MLs, and at least one switch controlled by the control circuitry and coupled between the internal node and another one of the arbiters.

According to an aspect of the present application, an ultrasound device is provided, comprising a semiconductor chip, multiline processing units (MLS) integrated on the semiconductor chip and configured to process channels of ultrasound data to produce multilines, and multiple power islands, wherein the MLs comprise multiple groups of MLs, and each of the multiple groups of MLs is implemented in a different one of the multiple power islands.

According to an aspect of the present application, a method of operating an ultrasound device is provided, the method comprising receiving, with control circuitry, an indication to configure the ultrasound device in a first configuration that includes outputting m1 multilines per channel of ultrasound data and processing n1 channels of ultrasound data channels per processing cycle, configuring the ultrasound device in the first configuration, receiving, with the control circuitry, an indication to configure the ultrasound device in a second configuration that includes outputting m2 multilines per channel of ultrasound data and processing n2 channels of ultrasound data channels per processing cycle, wherein m2 is greater than m1 and n2 is less than n1 or m2 is less than m1 and n2 is greater than n1, and configuring the ultrasound device in the second configuration.

In some embodiments, the method may further include receiving, with arbiter circuitry of the ultrasound device, multiple channels of ultrasound data, and processing, with multiline processing units (MLs) of the ultrasound device, channels of ultrasound data to produce multilines, and wherein configuring the ultrasound device in the first and/or second configurations comprises controlling which of the multiple channels of ultrasound data the arbiter circuitry outputs to which of the MLs on which processing cycle.

In some embodiments, the method may further include disabling certain of the MLs with the control circuitry.

In some embodiments, the method may further include outputting, with the control circuitry, parameters to the MLs, wherein the parameters control focusing of each of the MLs on particular points in space.

In some embodiments, the arbiter circuitry comprises multiplexers, and the method further comprises receiving as inputs, with each of the multiplexers, each of the multiple channels of ultrasound data, and outputting, with each of the multiplexers, one of the multiple channels of ultrasound data to a respective group of the MLs, wherein the method further comprises, when controlling which of the multiple channels of ultrasound data the arbiter circuitry outputs to which of the MLs on which processing cycle, controlling, with the control circuitry, each of the multiplexers to output a particular one of the multiple channels of ultrasound data to that multiplexer's respective group of the MLs on a particular processing cycle.

In some embodiments, the arbiter circuitry comprises arbiters, each of the arbiters is configured to receive a respective one of the multiple channels of ultrasound data from circuitry external to the arbiter circuitry, and the method further comprises, when the control circuitry is controlling which of the multiple channels of ultrasound data the arbiter circuitry outputs to which of the MLs on which processing cycle controlling each of the arbiters, on a particular processing cycle, to perform one, both, or none of: receiving a particular one of the multiple channels of ultrasound data from another one of the arbiters; and outputting a particular one of the multiple channels of ultrasound data received either from the circuitry external to the arbiter circuitry or from another arbiter to one or more other of the arbiters; and controlling each of the arbiters to output to a respective group of the MLs on the particular processing cycle: the respective one of the multiple channels of ultrasound data received from the circuitry external to the arbiter circuitry; or one of the multiple channels of ultrasound data received from another one of the arbiters.

In some embodiments, the control circuitry, the arbiter circuitry, and the MLs are integrated in a semiconductor chip.

In some embodiments, the semiconductor chip further comprises multiple power islands, the MLs comprise multiple groups of MLs, and each of the multiple groups of MLs is implemented in a different one of the multiple power islands.

In some embodiments, a number of the multiple groups of MLs is equal to a number of the multiple ultrasound data channels.

In some embodiments, when n2 is less than n1: n1 is 2 and n2 is 1, n1 is 4 and n2 is 2, n1 is 4 and n2 is 1, n1 is 8 and n2 is 4, n1 is 8 and n2 is 2, or n1 is 8 and n2 is 1; and when n2 is greater than n1: n1 is 1 and n2 is 2, n1 is 2 and n2 is 4, n1 is 1 and n2 is 4, n1 is 4 and n2 is 8, n1 is 2 and n2 is 8; or n1 is 1 and n2 is 8.

In some embodiments, receiving the indication to configure the ultrasound device in the first configuration comprises receiving the indication based on: a user selecting to image a particular anatomy; or an automatic selection to image a particular anatomy.

In some embodiments, the first configuration is a configuration for imaging the heart; the second configuration is a configuration for imaging the abdomen; and m2 is greater than m1 and n2 is less than n1.

In some embodiments, the first configuration is a configuration for imaging the abdomen; the second configuration is a configuration for imaging the heart; and m2 is less than m1 and n2 is greater than n1.

According to an aspect of the present application, a method of operating an ultrasound device is provided, the method comprising: receiving multiple channels of ultrasound data with arbiter circuitry; processing channels of ultrasound data with multiline processing units (MLs) to produce multilines; and controlling, with control circuitry, which of the multiple channels of ultrasound data the arbiter circuitry outputs to which of the MLs on which processing cycle.

In some embodiments, the method further includes disabling certain of the MLs with the control circuitry.

In some embodiments, the method further includes outputting, with the control circuitry, parameters to the MLs, the parameters controlling focusing of each of the MLs on particular points in space.

In some embodiments, the arbiter circuitry comprises multiplexers; and the method further comprises, with each of the multiplexers: receiving as inputs each of the multiple channels of ultrasound data; and outputting one of the multiple channels of ultrasound data to a respective group of the MLs; the method further comprising, when controlling which of the multiple channels of ultrasound data the arbiter circuitry outputs to which of the MLs on which processing cycle, controlling each of the multiplexers to output a particular one of the multiple channels of ultrasound data to that multiplexer's respective group of the MLs on a particular processing cycle.

In some embodiments, the arbiter circuitry comprises arbiters, and the method further comprises receiving, with each of the arbiters, a respective one of the multiple channels of ultrasound data from circuitry external to the arbiter circuitry; and when controlling which of the multiple channels of ultrasound data the arbiter circuitry outputs to which of the MLs on which processing cycle: controlling each of the arbiters, on a particular processing cycle, to perform one, both, or none of: receiving a particular one of the multiple channels of ultrasound data from another one of the arbiters; and outputting a particular one of the multiple channels of ultrasound data received either from the circuitry external to the arbiter circuitry or from another arbiter to one or more other of the arbiters; and controlling each of the arbiters to output to a respective group of the MLs on the particular processing cycle: the respective one of the multiple channels of ultrasound data received from the circuitry external to the arbiter circuitry; or one of the multiple channels of ultrasound data received from another one of the arbiters.

In some embodiments, each of the arbiters comprises an internal node. a switch coupled between the internal node and the respective one of the multiple channels of ultrasound data received from circuitry external to the arbiter circuitry, a switch coupled between the internal node and the respective group of the MLs; and at least one switch coupled between the internal node and another one of the arbiters.

G7. The method of claim G1, wherein the control circuitry, the arbiter circuitry, and the MLs are integrated in a semiconductor chip.

In some embodiments, the semiconductor chip further comprises multiple power islands, the MLs comprise multiple groups of MLs, and each of the multiple groups of MLs is implemented in a different one of the multiple power islands.

In some embodiments, a number of the multiple groups of MLs is equal to a number of the multiple ultrasound data channels.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
- a semiconductor substrate including a plurality of power islands, wherein each of the power islands is independently powered;
- multiline processing units (MLs) formed on the semiconductor substrate and configured to process channels of ultrasound data to produce multilines, the MLs including multiple groups of MLs each of which is implemented in a different power island of the plurality of power islands; and
- control circuitry formed on the semiconductor substrate and configured to control which of the MLs receive ultrasound data and to power on and off one or more power islands of the plurality of power islands.

2. The ultrasound device of claim 1, wherein the control circuitry is further configured to:
- receive an indication to configure the ultrasound device in one configuration of a plurality of configurations that includes outputting a selected number of multilines per channel of the ultrasound data; and
- power on one or more power islands of the plurality of power islands used for the configuration while maintaining other power islands in a powered off state.

3. The ultrasound device of claim 2, wherein the plurality of configurations include:
- a first configuration that includes outputting a first number of multilines per channel of ultrasound data and processing a first number of channels of ultrasound data channels per processing cycle; and
- a second configuration that includes outputting a second number of multilines per channel of ultrasound data and processing a second number of channels of ultrasound data channels per processing cycle, wherein the first and second numbers of multilines and channels are different.

4. The ultrasound device of claim 3, wherein the first configuration is used for imaging the heart.

5. The ultrasound device of claim 3, wherein the second configuration is used for imaging the abdomen.

6. The ultrasound device of claim 1, wherein the control circuitry is further configured to control focusing of each of the MLs on a particular point in space.

7. The ultrasound device of claim 1, further comprising:
- arbiter circuitry formed on the semiconductor substrate and configured to:
  - receive multiple channels of the ultrasound data; and
  - output a portion of the multiple channels of the ultrasound data to one or more MLs under control of the control circuitry.

8. The ultrasound device of claim 7, wherein:
- the arbiter circuitry includes multiplexers, each of the multiplexers configured to:
  - receive as inputs each of the multiple channels of ultrasound data; and
  - output one of the multiple channels of ultrasound data to a respective group of the MLS;
- wherein the control circuitry is configured, when controlling which of the multiple channels of ultrasound data the arbiter circuitry outputs to which of the MLs, to control each of the multiplexers to output a particular one of the multiple channels of ultrasound data to that multiplexer's respective group of the MLs.

9. The ultrasound device of claim 7, wherein:
- the arbiter circuitry includes arbiters, each of the arbiters configured to receive a respective one of the multiple channels of ultrasound data from circuitry external to the arbiter circuitry; and
- the control circuitry is configured, when controlling which of the multiple channels of ultrasound data the arbiter circuitry outputs to which of the MLs on which processing cycle, to control each of the arbiters to output to a respective group of the MLs at least one of:
  - the respective one of the multiple channels of ultrasound data received from the circuitry external to the arbiter circuitry; or
  - one of the multiple channels of ultrasound data received from another one of the arbiters.

10. The ultrasound device of claim 9, wherein the control circuitry is further configured, when controlling which of the multiple channels of ultrasound data the arbiter circuitry outputs to which of the MLs, to control each of the arbiters to at least one of:
- receiving a particular one of the multiple channels of ultrasound data from another one of the arbiters; or
- outputting a particular one of the multiple channels of ultrasound data received either from the circuitry external to the arbiter circuitry or from another arbiter to one or more other of the arbiters.

11. A method for controlling an ultrasound device, the method comprising:
- transmitting ultrasound data to multiline processing units (MLs) formed on a semiconductor substrate including a plurality of power islands, wherein each of the power islands is independently powered, the MLs configured to process channels of ultrasound data to produce multilines, the MLs including multiple groups of MLs each of which is implemented in a different power island of the plurality of power islands; and
- controlling, using control circuitry formed on the semiconductor substrate, which of the MLs receive ultrasound data and to power on and off one or more power islands of the plurality of power islands.

12. The method of claim 11, further comprising:
- receiving at the control circuitry an indication to configure the ultrasound device in one configuration of a plurality of configurations that includes outputting a selected number of multilines per channel of the ultrasound data; and powering on one or more power islands of the plurality of power islands used for the configuration while maintaining other power islands in a powered off state.

13. The method of claim 12, wherein the plurality of configurations include:

a first configuration that includes outputting a first number of multilines per channel of ultrasound data and processing a first number of channels of ultrasound data channels per processing cycle; and a second configuration that includes outputting a second number of multilines per channel of ultrasound data and processing a second number of channels of ultrasound data channels per processing cycle, wherein the first and second numbers of multilines and channels are different.

14. The method of claim 13, wherein the first configuration is used for imaging the heart.

15. The method of claim 13, wherein the second configuration is used for imaging the abdomen.

16. The method of claim 11, further comprising controlling focusing of each of the MLs on a particular point in space.

17. The method of claim 11, further comprising:

receiving multiple channels of the ultrasound data at arbiter circuitry formed on the semiconductor substrate; and outputting a portion of the multiple channels of the ultrasound data to one or more MLs under control of the control circuitry.

18. The method of claim 17, further comprising:

receiving as inputs each of the multiple channels of ultrasound data at a corresponding multiplexer of multiplexers of the arbiter circuitry; and outputting one of the multiple channels of ultrasound data from the multiplexers to a respective group of the MLs, wherein the control circuitry is configured, when controlling which of the multiple channels of ultrasound data the arbiter circuitry outputs to which of the MLs, to control each of the multiplexers to output a particular one of the multiple channels of ultrasound data to that multiplexer's respective group of the MLs.

19. The method of claim 17, further comprising:

receiving as inputs each of the multiple channels of ultrasound data at a corresponding arbiter of arbiters of the arbiter circuitry from circuitry external to the arbiter circuitry, wherein the control circuitry is configured, when controlling which of the multiple channels of ultrasound data the arbiter circuitry outputs to which of the MLs on which processing cycle, to control each of the arbiters to output to a respective group of the MLs at least one of:

the respective one of the multiple channels of ultrasound data received from the circuitry external to the arbiter circuitry; or one of the multiple channels of ultrasound data received from another one of the arbiters.

20. The method of claim 19, wherein the control circuitry is further configured, when controlling which of the multiple channels of ultrasound data the arbiter circuitry outputs to which of the MLs, to control each of the arbiters to at least one of:

receiving a particular one of the multiple channels of ultrasound data from another one of the arbiters; and outputting a particular one of the multiple channels of ultrasound data received either from the circuitry external to the arbiter circuitry or from another arbiter to one or more other of the arbiters.

* * * * *